United States Patent [19]
Koganty et al.

[11] Patent Number: 5,527,891
[45] Date of Patent: Jun. 18, 1996

[54] STEREODIRECTED PROCESS FOR SYNTHESIS OF α-N-ACETYLGALACTOSAMINIDES

[75] Inventors: R. Rao Koganty; Sham Gandhi, both of Edmonton, Canada

[73] Assignee: Biomira, Inc., Edmonton, Canada

[21] Appl. No.: 208,268

[22] Filed: Mar. 9, 1994

[51] Int. Cl.⁶ ............................. C07H 5/06; C07H 5/04; C07H 1/00
[52] U.S. Cl. ................................. 536/17.400; 536/18.6; 536/55.2; 536/55.3; 536/124
[58] Field of Search ................... 536/17.4, 18.6, 536/55.2, 55.3, 124

[56] References Cited

U.S. PATENT DOCUMENTS

| | | | |
|---|---|---|---|
| 4,195,174 | 3/1980 | Lemieux et al. | 536/53 |
| 4,308,376 | 12/1981 | Lemieux et al. | 536/53 |
| 4,362,720 | 12/1982 | Lemieux et al. | 536/53 |
| 4,794,176 | 12/1988 | Lemieux et al. | 536/53 |
| 4,866,045 | 12/1989 | Tieman | 514/144 |
| 4,935,503 | 6/1990 | Naicker et al. | 536/17.2 |

FOREIGN PATENT DOCUMENTS 8908711  9/1989  WIPO.

OTHER PUBLICATIONS

Bencomo et al, *Synthesis of glycopeptides having clusters of O–glycosylic disaccharide chains [β–D–Gal–(1→3)–α–D–GalNAc] located at vicinal amino acid residues of the peptide chain*, Carbohydrate Research, vol. 116, pp. C9–C12, 1983.

Burchell et al, *Development and Characterization of Breast Cancer Reactive Monoclonal Antibodies Directed to the Core Protein of the Human Milk Mucin*, Cancer Research, vol. 47, pp. 5476–5482, Oct. 15, 1987.

Carraway et al, *Structural and functional aspects of tumor cell sialomucins*, Molecular And Cellular Bio-Chemistry, vol. 72, pp. 109–110, 1986.

Evans et al, *Acetal Exchange Reactions*, Carbohydrate Research, vol. 3, pp. 453–462, 1967.

Ferrari et al, *The synthesis of derivatives of 3–O–(2–acetamido–2–deoxy–α–D–galactopyranosyl)–L–serine and –L–threonine*, Carbohydrate Research, vol. 79, pp. C1–C7, 1980.

Ferrari et al, *Artificial Carbohydrate Antigens: The Synthesis of Glycopeptidic Haptens with $T_N$ Specificity*, Bioorganic Chemistry, vol. 11, pp. 85–95, 1982.

Filipe et al, *Mucins in the Human Gastrointestinal Epithelium: A Review*, Invest. Cell Pathol., vol. 2, pp. 195–216, 1979.

Florey et al, *Mucus Secretion in the Trachea*, British Journal of Experimental Pathology, vol. 13, No. 3, pp. 269–284, 1932.

Flowers et al, *Synthesis of 2–Acetamido–2–deoxy–3–O–(β–D–galactopyranosyl)–α–D–Galactose*, J. Org. Chem, vol. 30, pp. 2041–2043, Jun. 1965.

Gottschalk et al, *Studies on Mucoproteins*, Biochim. Biophys. Acta, vol. 54, pp. 226–235, 1961.

(List continued on next page.)

Primary Examiner—Michael G. Wityshyn
Assistant Examiner—Everett White
Attorney, Agent, or Firm—Iver P. Cooper

[57] ABSTRACT

A stereodirected process for synthesizing α-N-acetylgalactosaminides from N-acetylgalactosamine which, in a preferred embodiment, comprises:

reacting N-acetylgalactosamine with a dialkyl acetal of an aldehyde or ketone to form a 4,6-O-alkylidene derivative;

reacting said 4,6-O-alkylidene derivative with a protecting group compound to attach a protecting group selectively to 3-OH of said derivative to form a 3-O-protected derivative;

reacting said 3-O-protected derivative with an anomeric group to form a glycosyl donor;

reacting said glycosyl donor with an alcohol to form an N-acetylgalactosaminide.

10 Claims, 17 Drawing Sheets

OTHER PUBLICATIONS

Hakomori, *Aberrant Glycosylation in Tumors and Tumor-Associated Carbohydrate Antigens*, Advances in Cancer Research, vol. 52, pp. 257–331, 1989.

Hanisch et al, *A B72.3 Second-Generation-Monoclonal Antibody (CC49) Defines the Mucin-Carried Carbohydrate Epitope Galβ(1–3)[NeuAca(2–6)]GalNAc*, Biol. Chem. Hoppe Seyler, vol. 370, pp. 21–26, 1989.

Hill et al, *Purification, Composition, Molecular Weight, and Subunit Structure of Ovine Submaxillary Mucin*, The Journal of Biological Chemistry, vol. 252, No. 11, pp. 3791–3798, Jun. 10, 1977.

Hull et al, *Oligosaccharide Differences in the DF3 Sialomucin Antigen from Normal Human Milk and the BT-20 Human Breast Carcinoma Cell Line*, Cancer Communications, vol. 1, No. 4, pp. 261–267, 1989.

Iijima et al, *Synthesis of a Mucin-Type O-Glycosylated Amino Acid β-Gal-(1—3)-[a-Ncu5Ac-(2—6)-a-GalNAc-(1—3)-Ser*, Carbohydrate Research, vol. 186, pp. 95–106, 1989.

Itzkowitz et al, *Sialosyl-Tn, A Novel Mucin Antigen Associated with Prognosis in Colorectal Cancer Patients*, Cancer, vol. 66, pp. 1960–1966, Nov. 1, 1990.

Jerome et al, *Cytotoxic T-Lymphocytes Derived from Patients with Breast Adenocarcinoma Recognize an Epitope Present on the Protein Core of a Mucin Molecule Preferentially Expressed Malignant Cells*, Cancer Research, vol. 51, pp. 2908–2916, 1991.

Lemieux et al, *The azidonitration of tri-O-accetyl-D-galactal*, Can. J. Chem., vol. 57, pp. 1244–1251, 1979.

Maclean et al, *Immunization of breast cancer patients using a synthetic sialyl-Tn glycoconjugate plus Detox adjuvant*, Cancer Immunol Immunother, vol. 36, pp. 215–222, 1993.

Maclean et al, *Active Immunization of Human Ovarian Cancer Patients Against a Common Carcinoma (Thomsen-Friedenreich) Determinant Using a Synthetic Carbohydrate Antigen*, Journal of Immunotherapy, vol. 11, No. 4, pp. 292–305, 1992.

Marchesi et al, *The Red Cell Membrane*, Ann. Rev. Biochem., vol. 45, pp. 667–698, 1976.

Orntoft et al, *O-Linked Mucin-Type Glycoproteins in Normal and Malignant Colon Mucosa: Lack of T-Antigen Expression and Acumulation of Tn and Sialosyl-Tn Antigens in Carcinomas*, Int. J. Cancer, vol. 45, pp. 666–672, 1990.

Paulsen et al, *Synthese a-glycosidisch verknupfter disaccharide der 2-Amino-2-desoxy-D-galactopyranose*, Chem. Ber., vol. 111, pp. 2358–2363, 1978.

Paulsen et al, *Synthese Der Clycopeptide O-β-D-Galactopyranosyl-(1—3)-L-Serin und-L-Threoonin*, Carbohydrate Research, vol. 109, pp. 89–107, 1982.

Podolsky, *Oligosaccharide Structures of Human Colonic Mucin*, The Journal of Biological Chemistry, vol. 260, No. 14, pp. 8262–8271, Jul. 15, 1985.

Roussel et al, *The complexity of mucins*, Biochimie, vol. 70, pp. 1471–1482, 1988.

Samuel et al, *Human Tumor Associated TF Antigen*, Cancer Research, vol. 50, pp. 4801–4808, 1990.

Schmidt et al, *Facile Synthesis of a- and β-O-Glycosyl Imidates; Preparation of Glycosides and Disaccharides*, Angew. Chem. Int. Ed. Engl., vol. 19, No. 9, pp. 731–732, 1980.

Simmons et al, *Molecular Cloning of a cDNA Encoding CD34, A Sialomucin of Human Hematopoietic Stem Cells*, The Journal of Immunology, vol. 148, No. 1, pp. 267–271, Jan. 1, 1992.

Springer, *T and Tn, General Carcinoma Autoantigens*, Science, vol. 224, pp. 1198–1204, 1984.

Yonezawa et al, *Sialosyl-Tn Antigen, Its Distribution in Normal Human Tissues and Expression in Adenocarcinomas*, Anatomic Pathology, vol. 98, No. 2, pp. 167–174, Aug. 1992.

2a

2b

2c

2d

2e

3a

3b

3c

3d

3e

4a

4b

4c

4d

4e

4f

4g

4h

5a, $R_1$ = H, $R_2$ = Bz
5b, $R_1$ = $CH_3$, $R_2$ = Bz
5c, $R_1$ = H, $R_2$ = Ac
5d, $R_1$ = $CH_3$, $R_2$ = Ac

6a, R = H
6b, R = $CH_3$

7a, R₁=H, R₂=Bz
7b, R₁=CH₃, R₂=Bz
7c, R₁=H, R₂=Ac
7d, R₁=CH₃, R₂=Ac

8a, R = H
8b, R = CH₃

9a, R=H
9b, R=CH₃

10a, R=H
10b, R=CH₃

11a, R=H
11b, R=CH₃

12a, R=H
12b, R=CH₃

13a, R₁ = H, R₂ = Bz
13b, R₁ = CH₃, R₂ = Bz
13c, R₁ = H, R₂ = Ac
13d, R₁ = CH₃, R₂ = Ac

14a, R = H
14b, R = CH₃

15a, R = H
15b, R = CH₃

16a, R = H
16b, R = CH₃

17a, R=H
17b, R=CH₃

18a, R=H
18b, R=CH₃

19a, R = H
19b, R = CH₃

20a, R = H
20b, R = CH₃

21a, R = H
21b, R = CH₃

22a, R = H
22b, R = CH₃

23a, R = H
23b, R = CH₃

24a, R = H
24b, R = CH₃

STEREODIRECTED PROCESS FOR SYNTHESIS OF α-N-ACETYLGALACTOSAMINIDES

BACKGROUND OF THE INVENTION

1. Field of the Invention

The present invention relates to the synthesis of biologically important α-glycosides of N-acetylgalactosamine, and provides versatile new intermediates for an improved method of preparing oligosaccharides, glycosylamino acids, and glycopeptides which are useful in treating and diagnosing cancers as well as other disease states.

2. Description of the Background Art

Mucins are glycoproteins found in saliva, gastric juices, and the like that form viscous solutions and act as lubricants or protectants on external and internal body surfaces (Florey, et al., *Br. J. Exp. Pathol.*, 13: 269, 1932; Gottschalk, et al., *Glycoproteins: Their Composition, Structure and Function*, Gottschalk, A., Ed., Elsevier, New York, 1972; Gottschalk, et al., *Biochem. Biophys. Acta*, 54: 226, 1961; Hill, et al., *J. Biol. Chem.*, 252: 3791, 1977; Roussel, et al., *Biochimie*, 70: 1471, 1988). Mucins are of typical high molecular weight compounds, often greater than 100,000 Daltons, and are extensively glycosylated (up to 80% glycan).

Mucin glycans (Podolsky, *J. Biol. Chem.*, 260: 8262, 1985) are bound to the "core" protein (or apaproteini) of the mucin through oxygen atoms in the side chains of serine and/or threonine residues. This is termed as an O-linkage. The reducing sugar of the glycan (the sugar directly attached to the core protein) is usually N-acetylgalactosamine (Stryer, *Biochemistry*, 3rd Edition, W. H. Freeman & Co., New York, 1988, p. 298). The main sugar constituents of the mucin glycans are galactose, N-acetylgalactosamine, N-acetylglucosamine, fucose, and sialic acid (Filipe, *Invest. Cell, Pathol.*, 2: 195, 1979).

Mucins are normally found in the secretions of many epithelial glands. However, they can also occur cell-bound as integral membrane proteins (Simmons, et al., *J. Immunol.*, 148: 267, 1992; Marchesi, et al., *Ann. Rev. Biochem.*, 45: 667, 1976; Carraway, et al., *Mol. Cell. Biochem.*, 72: 109, 1986).

Cancer-associated mucins are produced by tumor tissue of epithelial cell origin (Burcheil, et al., *Cancer Res.*, 47: 5476, 1987; Jerome, et al., *Cancer Res.*, 51: 2908, 1991). A major difference between the normal mucins and the aberrant, cancer-associated mucins, is in the structures of their respective glycans. The extent of glycosylation of cancer associated mucins is lower than that of their normal counterparts (Hull, et al., *Cancer Commun.*, 1:261, 1989). For example, while the normal mucin associated with human milk fat globules contains primarily the tetrasaccharide glycan, βGal 1–4 βGlcNAc 1–6(βGal 1–3)GalNAc and its sialylated analogs, the GlcNAc 1–6 transferase seems to be defective in breast cancer cells (Hull, et al., vide supra). As a result, the non reducing β1–4-linked galactosyl residue is also absent and the glycans of breast cancer-associated mucins are characteristically incomplete. Typical glycan structures found in cancer-associated mucins are the solitary N-acetylgalactosaminyl residue (Tn-determinant) or the disaccharide βGal 1–3 αGalNAc (T-determinant; Springer, *Science*, 224: 1198, 1984). In both the Tn and TF determinants, additional 2-6-linked α-sialyl groups may be attached to the N-acetylgalactosaminyl moiety, resulting in the sialyl-Tn (STn) and sialyl-2-6T determinants (Hanish, et al., *Biol. Chem. Hoppe-Seyler*, 370: 21, 1989; Hakomori, *Adv. Cancer Res.*, 52: 257, 1989; Oristoft, et al., *Int. J. Cancer*, 45: 666, 1980; Samuel, et al., *Cancer Res.*, 50: 4801, 1990).

More than 90% of primary carcinomas and their metastases contain the Tn and T determinants in immunoreactive form on their external surface membranes (Springer, vide suora). The altered glycan determinants displayed by the cancer-associated mucins are recognized as non-self or foreign by the patient's immune system, resulting in autoimmune responses.

The presence of Tn, TF, STn and sialyl 2-6TF-antigens on cancer cells and the autoimmune response to these structures have been used for diagnostic and therapeutic procedures. As cancer markers, Tn and TF permit early immunohistochemical detection and prognostication of the invasiveness of some carcinomas (Springer, vide supra). The presence of the sialyl-Tn hapten on tumor tissue has been identified as an unfavorable prognostic parameter (Itzkowitz, et al., *Cancer*, 66: 1960, 1990; Yonezawa, et al., *Am. J. Clin. Pathol.*, 98: 167, 1992).

Measurements of the autoimmune response directed against the Tn and TF determinants permit detection of carcinomas with greater sensitivity and specificity, earlier than has previously been possible. Also, the extent of expression of Tn and TF determinants often correlates with the degree of differentiation of carcinomas (Springer, vide supra).

The nature of the Tn, TF and STn structures as tumor-associated antigens has led to their use in active specific immunotherapy of cancers. Specifically, the Tn, TF and STn determinants have been chemically synthesized and attached to carrier proteins to form artificial antigens; these were administered to cancer patients in combination with cyclophosphamide and the Ribi DETOX® adjuvant (MacLean, et al., *J. Immunother.*, 11: 292, 1992; MacLean, et al., *Cancer Immunoth.*, 36: 215, 1993).

Synthesis of glycosylated amino acids has become an important field of carbohydrate chemistry. More recently, synthesis of glycosylated segments of mucins and glycoproteins that are associated with tumors, pathogens and viruses have become extremely important because of their ability to function as immunogens. These synthetic antigens are chemically well-defined and are easily purified. However, a major concern in any synthetic vaccine development is large scale manufacturing for commercial purposes. The key factors to successful large scale production are commercial availability of the raw materials, the number of synthetic steps, quantity and the types of by-products formed and overall yields.

Glycosides of the Tn and TF haptens, and of their sialylated analogs, have been synthesized and conjugated to proteins or synthetic peptide carriers for use in diagnostic and therapeutic applications (Lemieux, et al., U.S. Pat. Nos. 4,794,176; 4,308,376; 4,362,720 and 4,195,174; Treman, U.S. Pat. No. 4,866,045 *Can. J. Chem.*, 57: 1244, 1979). Alternatively, the tumor-associated carbohydrate antigens have been isolated from natural sources and used in immunotherapeutic applications (Kjeldsen, et al., International Patent Application PCT/US89/00966, published as WO 89/08711 Sep. 21, 1989). The synthetic glycosides used have generally involved an aglycon moiety from which reactive functionality, suitable for coupling, could be generated without altering the saccharide portion of the hapten glycoside. The 'activated' hapten glycosides were then reacted with amino groups of the proteins or peptide carriers to form an amide or a Schiff base linkage which is further reduced to an amine. However, the artificial antigens prepared in this manner do not comprise the natural carbohydrate-peptide linkages, and therefore they induce a response against the epitopes contained in both the saccharide as well as synthetic aglycon. To overcome this limitation, glycosyl amino acids have been synthesized by linking the Tn or TF haptens to protected serine or threonine derivatives; these were then assembled into glycosyl oligopeptides involving two, three or four amino acid residues (Paulsen, et al., *Carbohydr. Res.*, 109: 89, 1982; Bencomo, et al., *Carbohydr. Res.*, 116: C9, 1983; Iijima, et al., *Carbohydr. Res.*, 186: 95, 1989).

For the synthesis of the required α-N-acetylgalactosaminides of hydroxyamino acids, glycosyl donors directly derived from N-acetylgalactosamine are unsuitable because the acetamido group directs glycoside formation toward the β-anomeric configuration through the neighboring group participation, and gives rise to formation of side products such as oxazolines (1c). Indeed, direct use of N-acetylgalactosamine has only been described under the conditions of the Fischer glycosidation (Flowers, et al., *J. Org. Chem.*, 30: 2041, 1965). However, the Fisher glycosidation is limited to aglycons derived from aliphatic and aromatic primary alcohols, while hydroxy amino acids such as serine and threonine are unsuitable due to their instability at the reaction conditions.

To obtain practical quantities of α-N-acetylgalactosaminides of hydroxyamino acids, the art has heretofore relied on a circuitous route using 2-azido-2-deoxygalactose derivatives as glycosyl donors and precursors of the N-acetylgalactosaminyl residues. As distinct from the acetamido group, the 2-azido group of the corresponding glycosyl donors does not participate in the reactions at the anomeric center resulting in the formation of side products, such as oxazolidines. Following the glycosidation step, the 2-azido-2-deoxyglycosides must be reduced to the amino glycoside and N-acetylated. By this indirect technique, α-N-acetylgalactosaminides of hydroxy amino acids may be obtained (Paulsen, et al., Bencomo, et al., and Iijima et al, vide supra). The required 2-azido-2-deoxy-galactosyl halide donors may be obtained via azidonitration of D-galactal, according to the process of Lemieux in U.S. patents cited above, *Can. J. Chem.*, 57: 1244, 1979; or according to Paulsen, et al., (*Chem. Ber.* 111, 2358, 1978), starting from 1,6;2,3-dianhydro-D-talcpyranose. 2-Azido-2-deoxygalactopyranosyl halide intermediates may also be directly prepared by azidochlorination of D-galactal derivatives, as shown by Naicker, et al., (U.S. Pat. No. 4,935,503). All of these processes require relatively expensive starting materials, add several steps to the already lengthy syntheses, and are poorly adaptable to commercial-scale manufacturing of these important synthetic antigens. Therefore, a need exists for a shorter, more practical process to prepare glycosylamino acids in commercial quantities.

Earlier attempts to make α-glycosides of N-acetylgalactosamine with hydroxy amino acids involved the coupling of protected N-acetylgalactosamine donors with protected serine or threonine compounds under Koenigs-Knorr, using silver salt, or Helferich, using a mercuric salt as a catalyst. Both the Koenigs-Knorr and Helferich syntheses yield solely or predominantly β-glycosides (1,2-trans) when a participating group is present.

Ferrari and Pavia, in *Carbohydr. Res.* 79: c1–c7, 1980; *Biorg. Chem.*, 11: 82–85, 1982, reacted 3,4,6-triacetyl, 2-azido, D-galactosyl chloride, with a $C_2$ non-participating group, with serine or threonine derivatives in the presence of mercuric cyanide to give the corresponding α-glycosylamino acid in 66 and 45% yield, respectively. This method involves the laborious and circuitous synthesis of a 2-azido galactosyl donor prior to glycosidation. Paulsen and Holck, reporting in *Carbohydr. Res.*, 109: 89–108, condensed the same chloride with a serine derivative in the presence of silver carbonate, Drierire®, 4A molecular sieves and silver perchlorate in toluene/dichloromethane to give an 85% yield of glycoamino acid, the ratio of α to β being 19:1. The azido group in the glycosides can be converted to acetamido group by reduction to amino group and N-acetylation. The required conditions for reduction to the amino group further complicates the glycopeptide synthesis by removing the Fmoc group on the amino acid, which may also acetylate the amino acid rendering it unsuitable for glycopeptide synthesis.

Attempts to make use of trichloroacetimidate of 3,4,6 triacetyl N-acetylgalactosamine (Gandhi, et al., XV Intnl. Carb. Symp. Aug. 12–17, Yokohama, Japan, 1990) as a donor resulted mostly in the formation of oxazoline (1c) and a very poor yield of α-glycoside (α to β ratio of 1:5), which proved not to be commercially viable.

SUMMARY OF THE INVENTION

Synthetically, it is difficult to manipulate N-acetyl-D-galactosamine because of significant side reactions which prevent the formation of glycosyl donors in good yields. Once obtained, such donors give rise to formation of the desired α-glycosides in very poor yields. Much of the donor is prevented from forming a glycoside because of extensive participation of the N-acetyl group with the incoming anomeric carbonium ion, forming an oxazoline (1c) as a major byproduct.

The present inventors have discovered that a joint protecting group such as acetal or ketal at the 4,6-position of GalNAc facilitates the formation of an α-glycosidic linkage. This enables the direct use of N-acetylgalactosamine for the synthesis of tumor-associated carbohydrate structures such as Tn (αGalNAc-O-Ser/Thr), TF (βGall-3αGalNAc-O-Ser/Thr) and STn (αNANA2-6αGalNAc-O-Ser/Thr). In the invention, α-N-acetylgalactosamine derivatives containing 4,6-O-alkylidene groupings (FIG. 1) are directly and conveniently prepared from commercially available N-acetylgalactosamine, and are used for preparing α-N-acetylgalactosaminides stereoselectively and in good yields. The crystalline N-acetylgalactosamine intermediates are used for the preparation of glycosylamino acid derivatives suitable for their incorporation into glycopeptides, or for the preparation of oligosaccharide block derivatives which are in turn used to glycosylate protected hydroxyamino acids for incorporation into oligosaccharide-peptides. The process of the present invention provides a facile, commercial-scale access to pure glycopeptides which are useful in diagnosis, therapy, and prophylaxis of cancers as well as other disease states.

Once the 4,6-hydroxy functions of N-acetylgalactosamine are jointly protected through a cyclic acetal/ketal group, the resulting 1,3 diol can be selectively acylated (or otherwise protected) or another carbohydrate ring such as 2,3,4,6-tetraacetyl galactose can be introduced to form a disaccharide block. Under the reaction conditions of the present invention, the anomeric OH group remains untouched. The mono/disaccharide block of the N-acetyl-D-galactosamine is easily converted to a glycosyl donor such as a trichloroacetimidate (FIG. 3). The 4,6-cylic acetals, as glycosyl donors, seem to function differently from the peracetylated N-acetylgalactosamine donor, which latter compound undergoes very complex reactions.

There are many advantages to the process of the present invention, including but not limited to:

Higher overall glycosidation yields

Better ratio of α to β glycosides

Rapid access to the glycosyl donors

No need for post-glycosidation reduction of azido to N-acetyl group as is the case for 2-azidogalactosyl donors.

Compatibility of the glycamine acids with the procedures for glycopeptide synthesis using automated synthesizers.

In preferred embodiments, the following new compounds and methods are contemplated:

The 4,6-benzylidene and 4,6-naphthylidene derivatives of N-acetyl-D-galactosamine and a general process for the synthesis of 4,6-O-cyclic acetals and ketals (FIG. 1);

Protected N-acetyl-D-galactosamine derivatives, the 3-O-acyl or 3-O-extended (3e), 4,6-O-benzylidene and 4,6-O-naphthylidene derivatives (FIG. 2);

N-acetyl-α-D-galactosaminyl-O-N(Fmoc) amino acid phenacyl ester (FIG. 4);

3-O-acyl 4,6-O-benzylidene/naphthylidenyl fluoride, chloride, phosphite and trichloracetimidate of N-acetyl-D-galactosamine (FIG. 3).

Other compounds of the present invention are shown in FIG. 11.

BRIEF DESCRIPTIONS OF THE DRAWINGS

FIGS. 1A to 1E: Shows the 4,6-Hydroxy protected cyclic acetyl/ketal structures (2a–2e) of N-acetyl-D-galactosamine.

FIGS. 2A to 2E: Shows selectively 3-OH protected structures (3a–3d) or 3-O-extensions of carbohydrate synthesis to a disaccharide (3e).

FIG. 3A(1)–3A(4) and 3B(1)–3B(4): Show the various glycosyl donors. Compounds 4a–4d appear in FIGS. 3A(1)–3A(4) and 4e–4h in FIGS. 3B(1)–3B(4).

FIGS. 4A and 4B: Show fully protected glycosylated amino acids, serine and threonine (compounds 5a–5d and 6a–6b).

FIGS. 5A and 5B: Show partial deprotection at 4,6 positions for further extension of synthesis. Compounds depicted are 7a–7d and 8a–8b.

FIGS. 6A–6D: Show structures derived through the extension of synthesis at 6-OH through sialylation. Compounds 9a, 9b, 10a, 10b, 11a, 11b, 12a and 12b are shown.

FIGS. 7A-1-7A-4: Shows the structures with amino acid carboxyl deprotected so that glycopeptide can be synthesized in an automated peptide synthesizer. Compounds 13a–13d, 14a, 14b, 15a, 15b, 16a and 16b are shown in FIG. 7A, and compounds 17a, 17b, 18a and 18b in FIG. 7B(1–7B(2).

FIGS. 8A(1)–8A(4) and 8B(1)–8B(2): Show completely deprotected synthetic carbohydrate haptens. Compounds 19a, 19b, 20a, 20b, 21a, 21b, 22a and 22b are in FIGS. 8A(1)–8A(4) and compounds 23a, 23b, 24a and 24b in FIG. 8B.

FIGS. 9A and 9B: Shows synthetic Scheme 1. Compounds 1, 2a, 3b, 4a, 5a, 13a and 19a appear in FIG. 9A, and compounds 5a, 7a, 9a, 20a and 15a in FIG. 9B.

FIGS. 10A and 10B: Shows synthetic Scheme 2. Compounds 2a, 3e, 4c, 6a, 14a, and 22a appear in FIG. 10A and compounds 6a, 8a, 11a, 23a and 17a in FIG. 10B.

FIGS. 11A and 11B: Shows generic structures A and C of compounds of the present invention.

FIGS. 12A and 12B: A Derivatization of GalNAc by reactions with (A) H⁺or (B) ZnCl₂.

DETAILED DESCRIPTION OF THE PREFERRED EMBODIMENTS

Figure 1A:
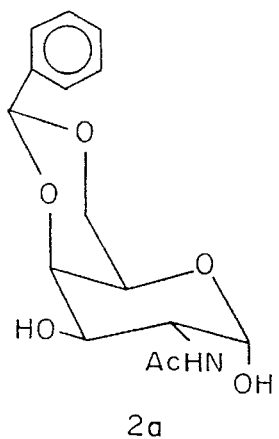
Figure 1B:
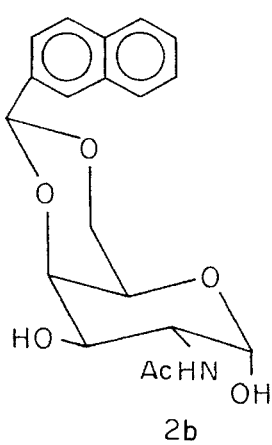
Figure 1C:
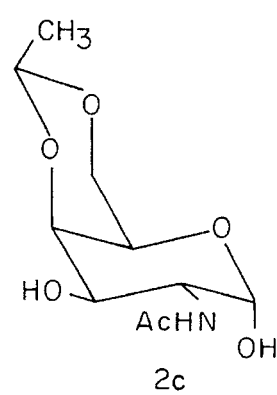
Figure 1D:
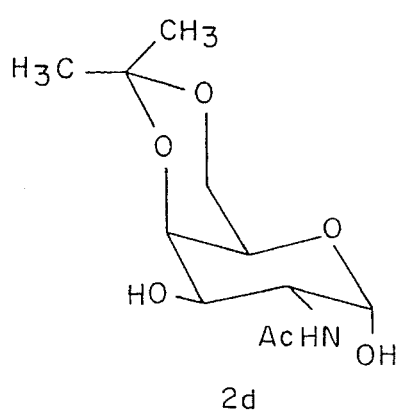
Figure 1E:
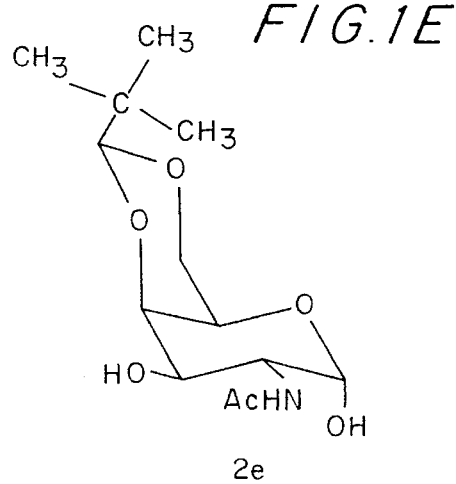
Figure 2A:
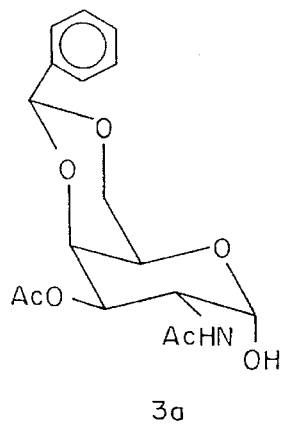
Figure 2B:
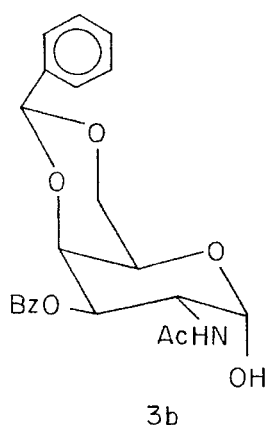
Figure 2C:
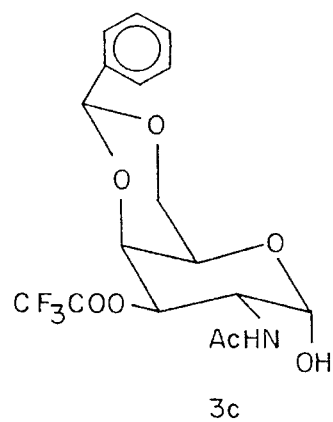
Figure 2D:
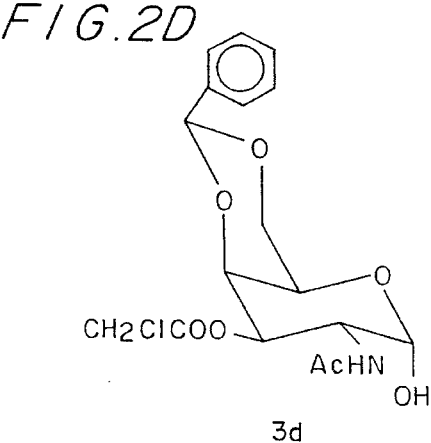
Figure 2E:
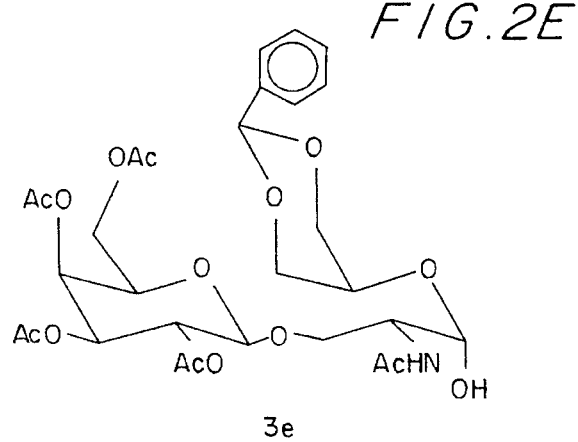

The present invention affords a superior process for commercial-scale production of artificial antigens representing the most important epitopes of cancer-associated mucins, namely, Tn, TF, STn and sialyl 2–6TF.

Additionally, the invention provides new intermediates for the convenient and economical preparation of artificial antigens.

The present invention relates to the discovery that derivatives of N-acetylgalactosamine in which the 4-O and 6-O positions are jointly protected by a bridging moiety are useful as glycosyl donors in the stereospecific synthesis of alpha-N-acetylgalactosaminides.

When alcohols are glycosylated using N-acetylgalactosamine-derived glycosyl donors containing a 4,6-O-alkylidene moiety, higher yields of α-glycosides are obtained. Typically, the yield of α-glycoside is 30–45%, while beta-glycosides are obtained at a level of 0–6%. In contrast, when peracetylated N-acetylgalactosmine-derived glycosyl donors are used, the yield of α-glycoside is only 4–5%, while β-glycoside recovery is of on the order of about 20%. Thus, there is usually at least a six-fold improvement in the absolute yield of α-glycoside, and normally at least a 20-fold improvement in the α/β ratio.

The present invention also substantially eliminates oxazoline formation. With peracetylated GalNAc reactions, the oxazoline production is about 45–50%. With the reaction of the present invention, oxazoline levels are about 0–3%.

Overall, the present invention provides a superior process for commercial scale production of mucin related glycopeptides and artificial antigens useful in the diagnosis, treatment, or prophylaxis of cancers End other disease states.

In a preferred embodiment, the process comprises preparing an α-glycoside of N-acetylgalactosamine by reacting a glycosyl acceptor with a glycosyl donor in which O-4 and O-6 of the N-acetylgalactosamine are linked into a 1,3-dioxane ring. More particularly, it involves (1) conversion of N-acetylgalactosamine into a 4,6-O-alkylidene derivative, (2) protection of the 3-O position; (3) conversion of the protected derivative into a glycosyl donor, and (4) glyosidation of a glycosyl acceptor.

Protection of the 4-O and 6-O Positions

The present invention contemplates derivatizing N-acetyl galactosamine for use as a glycosyl donor in a glycosidation reaction, by protecting the 4-O and 6-O positions with a joint protective group which inhibits participation of the N-acetyl group with the incoming anomeric carbonium ion.

The joint protecting group may be a 4,6-O alkylidene of the formula

where $R_1$ and $R_2$ are independently selected from the group consisting of hydrogen, alkyl (branched or unbranched, preferably 1–10 carbons), alkenyl, aryl (phenyl, naphthyl, etc.), heteroaryl (pyridyl, pyrolyl, quinolyl, etc.) and alkylaryl groups. $R_1$ and $R_2$ may be joined to form a cyclic system. The structure $O^4$—C (=CH Ph)—$O^6$ is also possible.

One or more hydrogen atoms of the aforementioned hydrocarbon groups may be replaced by a halogen, oxygen nitrogen or sulfur-related functional group.

N-acetylgalactosamine (1a) may be converted into a 4,6-O alkylidene derivatives (2a–e) by reacting N-acetylgalactosamine with a dialkyl acetal of an aldehyde or ketone in the presence of an acid catalyst, according to a method well-known in the art (cf. M. E. Evans, et al., *Carbohydr. Res.*, 3: 453, 1967). The most desired method is reacting N-acetylgalactosamine with benzaldehyde dimethylacetal to produce the 4,6-benzylidemfy, 4-acetylgalactosamine (2a).

Figure 12A:
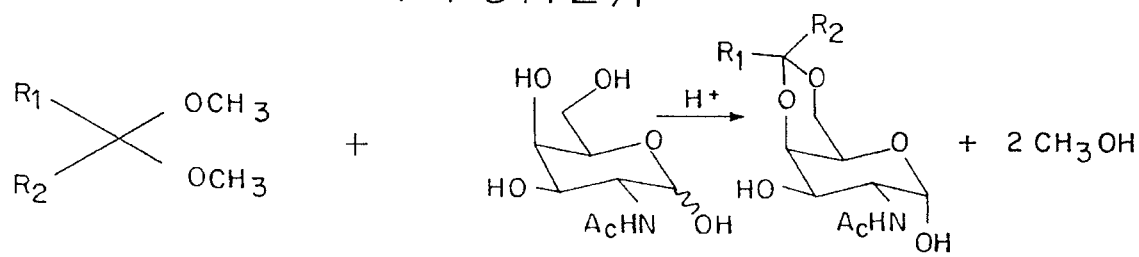
Figure 12B:
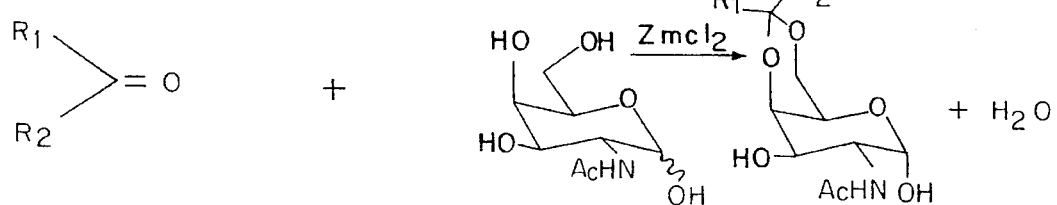

The preferred acid catalyst is p-toluene sulfonic acid, but any organic acid or inorganic acid in catalytic amounts should function similarly. The main function of the acid is to generate an aldehyde or keto group from the precursor reagent. The acid itself is not consumed since its function is simply to release the carbonyl group for the acetal/ketal formation. The same reaction is also brought about by a Lewis acid such as $ZnCl_2$, but in this case a carbonyl compound such as an aldehyde or ketone is used, instead of their alkoxy (usually methoxy) analogues. Many metal halides, such as halides of Al, Fe, Zn, Co etc., can function as Lewis acids with various degrees of efficiency. (See FIGS. 12A and 12B).

Protection of the 3-O-position

A large number of functionalities suitable for use as hydroxy protecting groups are known in the art, most notably in T. W. Greene, *Protecting Groups in Organic Synthesis,* John Wiley and Sons, Chapter 2, the protecting group chosen must satisfy the following characteristics: (1) it must be possible to use it to protect the 3-O position without substantially adversely affecting the joint protecting group at the 4,6-O-position, (2) it must substantially protect the 3-O position under the contemplated glycosidation conditions, and (3) they must be removable without substantially adversely affecting the resulting alpha-glycoside.

For the sake of clarity in nomenclature, when a hydroxyl group (—OH) is derivatized to form a protected hydroxy group (—OR), the protecting group is the "R". Typical protecting groups are $CH_3CO$—, $C_6H_5CO$—, $CH_2ClCO$—, and $CF_3CO$.

In a preferred embodiment, the protected group is a 3-O acylester derived from a carboxylic acid. 3-O-benzoyl is especially preferred. Thus, in the second step of the preferred process, a suitable protecting group is selectively attached to 3-O of the 4,6-O-alkylidene derivative, yielding, e.g., compounds 3a–3e.

The Glycosyl Donor

Figures 1, 3A:
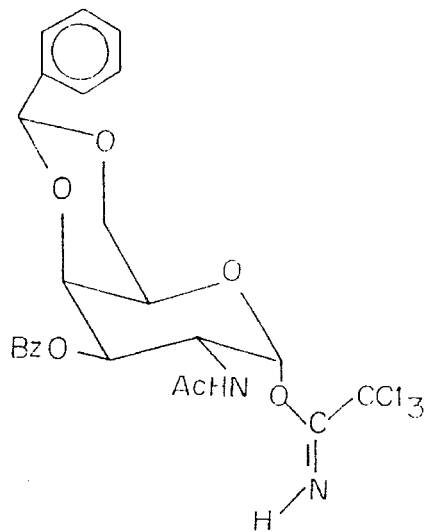
Figures 2, 3A:
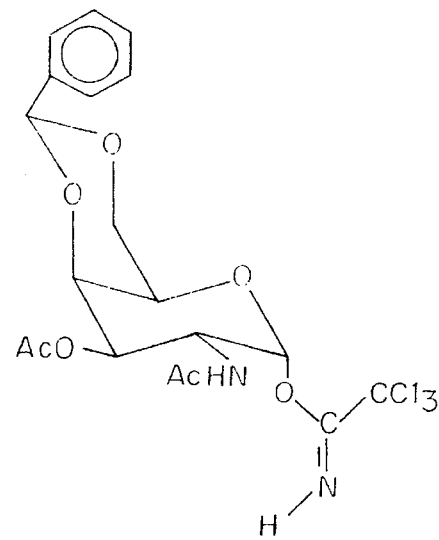
Figures 3, 3A:
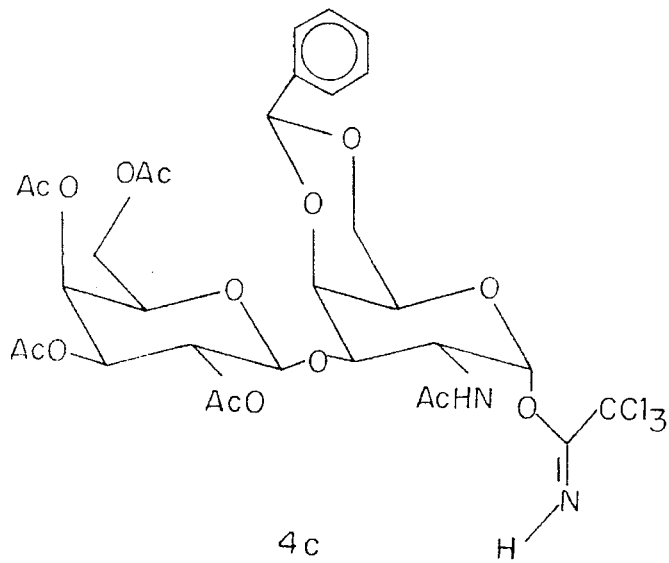

The 3-O-protected 4,6-O-alkylidene derivatives of N-acetylgalactosamine may be converted into glycosyl donors (FIG. 3), wherein the anomeric group is a potential leaving group such as a halide, a thioether, an ester group and the like. Even more preferred are donors containing an acetimidate leaving group, with trichloroacetimidate highly recommended (Schmidt, et al., *Angew Chem. Intern. Ed. Engl.,* 19: 732, 1980). Other leaving groups, which are as readily or more readily displaced than those mentioned above, may also be used, which are well known to those skilled in the art of organic synthesis.

Glycosylation

The third step of the process involves reacting the glycosyl donors (4a–e) with an alcohol such as serine or threonine (1d or 1e) to form α-N-acetyl-galactosaminides. The most preferred reactant alcohols are amino- and carboxy-protected derivatives of hydroxyamino acids, particularly those derived from serine (1d) or threonine (1e). Suitable amino- and carboxy-protecting groups are those generally known to be useful for protection of amino- and carboxyl group in peptide synthesis, such as acyl (formyl, trifluoroacetyl, phthalyl, benzyl, phenyl and the like); urethane (e.g., t-butyloxycarbonyl, p-methoxy benzyloxycarbonyl; 2-(p-biphenyl)-isopropyloxycarbonyl, isonicotinyloxycarbonyl, and the like); sulfenyl (O-nitro phenylsulfenyl, tritylsulfenyl, and the like); or alkyl (triphenylmethyl, benzhydryl, and the like). Preferred amino protecting groups are the 9-fluorenyl methoxycarbonyl (Fmoc) group and the tert-butoxycarbonyl (tBoc) group with Fmoc particularly preferred.

The methods of glycosylation used in the present invention are conventional methods, cf. Koenigs-Knorr, Acetimidate, trichloroacetimidate (Schmidt) method; iodide (Thiem), thio glycoside (Lönn). Many glycosidation reactions are known in the art. For reviews of the subject, see H. Paulsen, "Advances in selective chemical synthesis of complex oligosaccharides", *Angew. Chem. Intnl. Ed.,* 21, 155 (1982); R. R. Schmidt, "New methods for synthesis of glycosides and oligosaccharides. Are there alternatives to Koenigs-Knorr methods?", *Angew. Chem. Intnl.* 25, 212 (1986); H. Paulsen "Synthesis of complex oligosaccharide chains of glycoproteins", *Chem. Soc. Rev.* 13, 15 (1984); H. M. Flowers, "Chemical synthesis of oligosaccharides", *Methods in Enzymology* 138, 359 (1987).

As can be readily ascertained from the above cited literature, many reaction conditions for the glycosylation reactions are known. These conditions can readily be adjusted for individual reactions by one skilled in the art wished undue experimentation. In another aspect of the invention, the 4,6-O-alkylidene derivatives (2) are glycosylated at 3-OH to produce the reducing disaccharide derivatives (3e). In this case, the preferred glycosyl donors are peracetylated or perbenzylated pyranosyl halides, with 2,3, 4,6-tetra-O-acetylgalactosyl bromide being highly preferable. The glycosylations are performed using only a slight excess of donor so as to avoid glycosylation at 1-OH. The resulting reducing disaccharide derivatives (3e) are further processed to afford block disaccharide donors (4e) which, when reacted with alcohols, yield -glycosides. The alcohols for reaction with the block disaccharide donors are preferably amino- and carboxyl-protected derivatives of the hydroxyamino acids, particularly those of serine the threonine. The resulting α-glycosides bear the TF-determinant βGal 1–3 αGalNAc.

Carbohydrates and Glycopeptides

The α-N-acetylgalactosaminides of the present invention are useful as building blocks in the assembly of larger carbohydrates and of glycopeptides. The main purpose of this invention is the creation of a-linkage between the sugar and the aglycon. Once that is achieved, further synthesis can be carried out using the known art. In incorporating GalNAc into a larger carbohydrate (or glycopeptide), (1) the 4,6-O-protected GalNAc may be reacted at the 3-O position with another carbohydrate, which may be a mono-, or a di-, tri-, or other oligo-saccharide, and/or (2) the 3,4,6-O-protected GalNAc may be reacted at the 1-O position with another carbohydrate, which likewise may be a mono-, or a di-, tri- or other oligosaccharide.

If both reactions are desired, they may take place in either possible order. Subsequently, the protecting group for the hydroxyls of the 4-O and 6-O positions of the GalNAc may be removed, and other sugars linked to these positions.

Also, once a first sugar is linked to GalNAc, a second sugar may be linked to the first sugar. There are, of course, many possible synthetic combinations.

The linkages need not be limited to sugars, either. The glycosylamino acids prepared by the process of the present invention are useful in the synthesis of glycopeptides corresponding to particular structures of mucins such as cancer-associated mucins, including viral coat glycoproteins. Through the sequential removal-coupling removal cycles the glycosylamino acid derivatives are employed in methods of solid phase peptide synthesis. Using the glycosylamino acids prepared by the process of the present invention, such as serine and threonine, one can synthesize glycopeptides by using the glycosylated amino acids as building blocks in the FMOC (α-Fluorenyl methoxycarbonyl) based automated peptide synthesis, as well as by solid phase batch synthesis manually. Alternatively, glycopeptides can also be synthesized in solution phase using 1-butylchloroformate activation. The solid phase synthesis normally employs coupling agents such as dicyclohexyl carbodiimide and an activating agent for the carbonyl group, such as 1-hydroxybenzotriazole (HOBT) or N-Hydroxysuccinimide (NHS). However, these activating and coupling agents are merely illustrative of agents which can be used. One skilled in the art can refer to the literature for other known activating and coupling agents which can be used herein. These methods are well-known and are described in the following articles: Merrifield, *J. Amer. Chem. Soc.*, 85: 2149–2154, 1963; Merrifield, *Science*, 232: 341, 1986; Wade, et al., *Biopolymers*, 25: S21, 1986; Fields, *Int. J. Polypeptide Prot. Res.*, 35: 161, 1990; Millipore Report Nos. 2 and 2a, Millipore Corporation, Bedford, Mass., 1987.

Figures 3, 3A, 4:
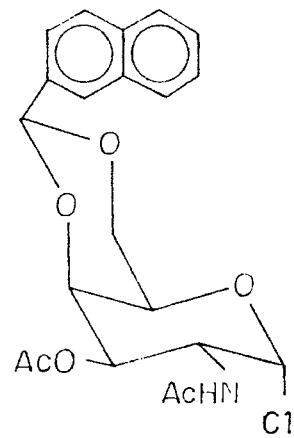
Figures 1, 3B:
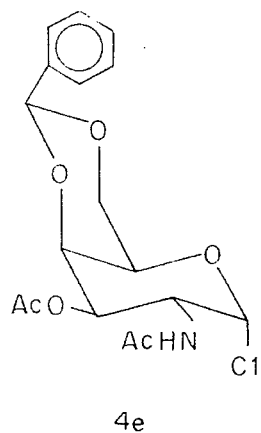
Figures 2, 3B:
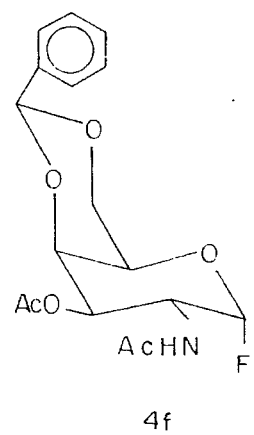
Figures 3, 3B:
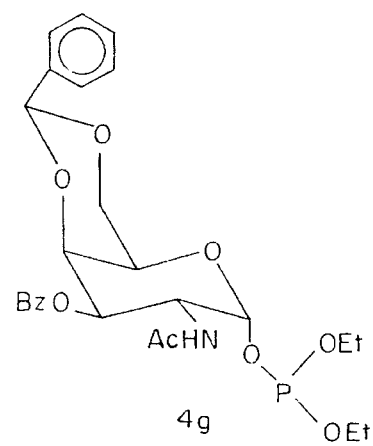
Figures 3, 3B, 4:
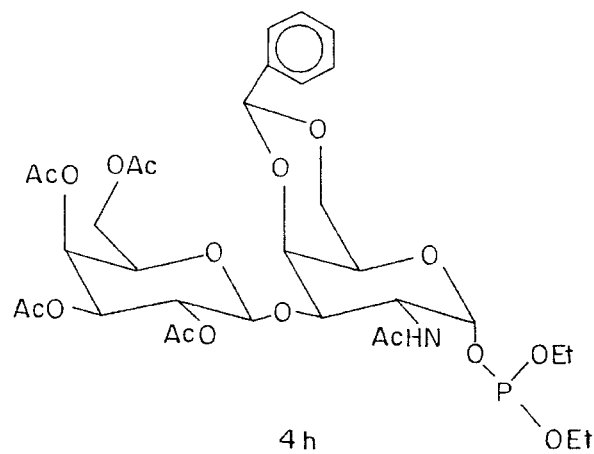
Figure 4A:
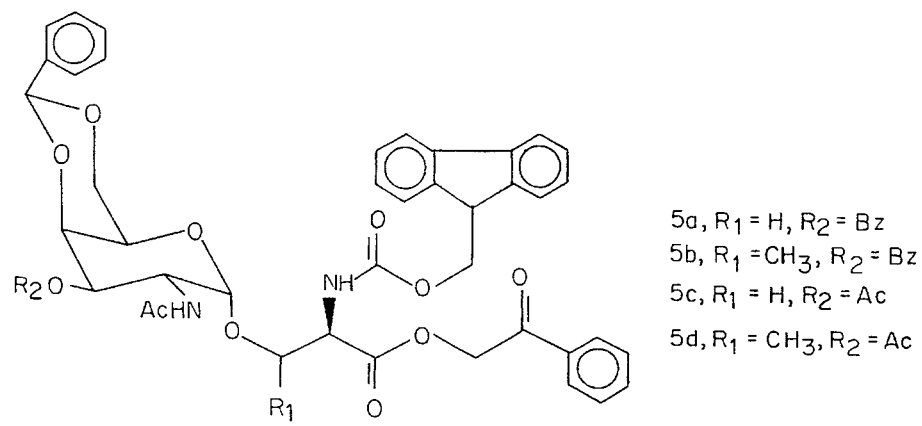
Figure 4B:
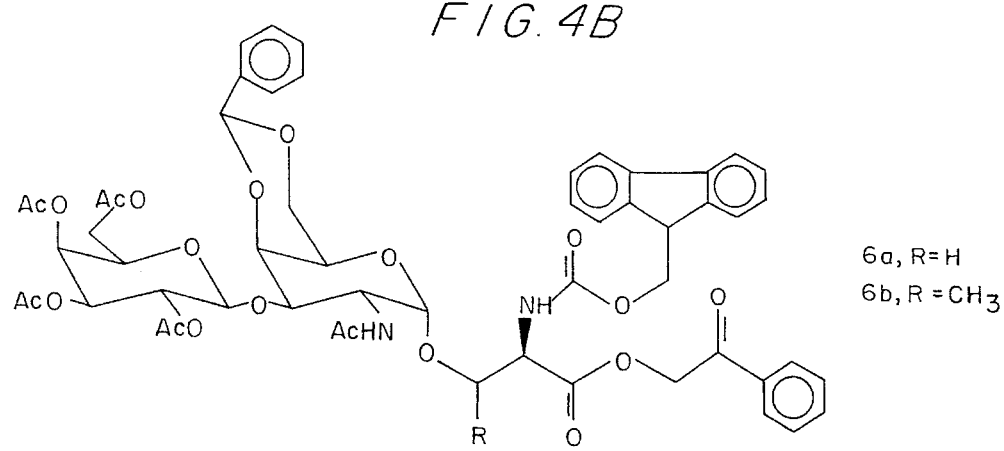
Figure 5A:
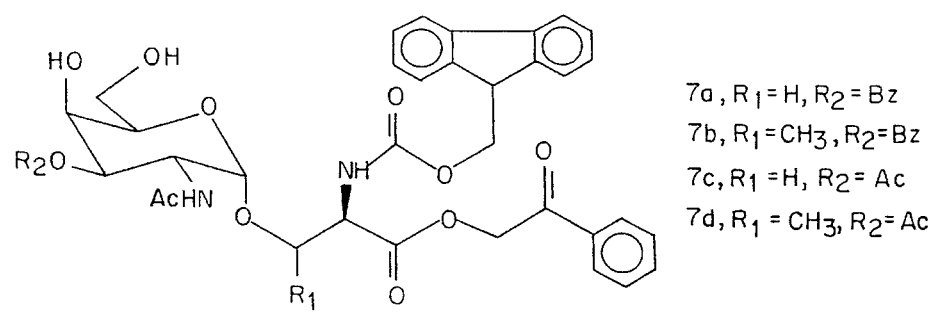
Figure 5B:
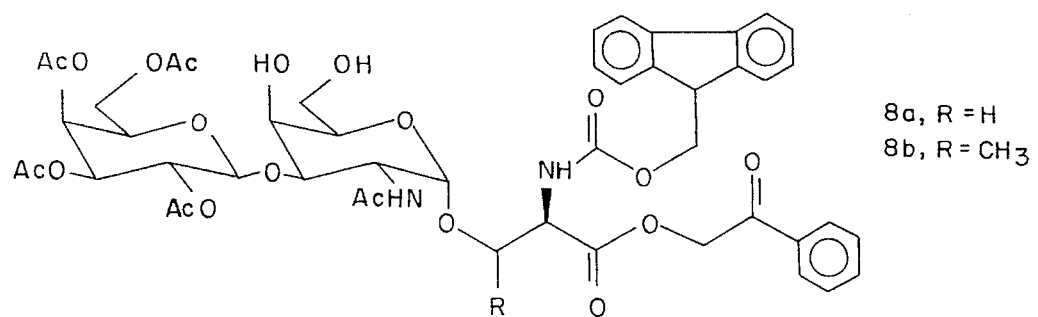
Figure 6A:
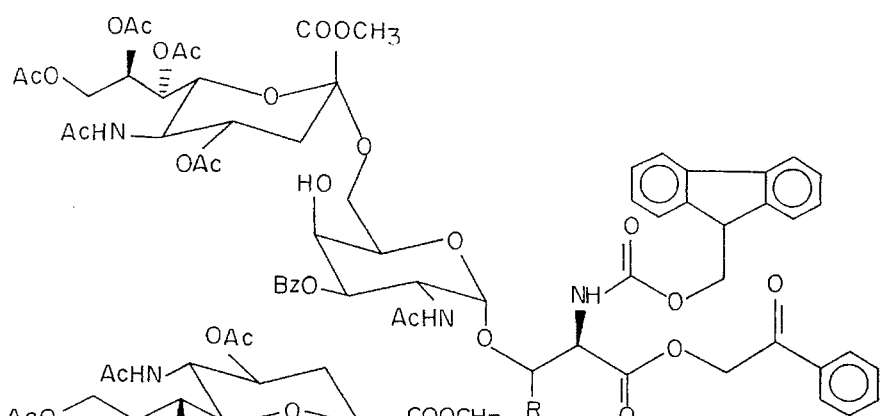
Figure 6B:
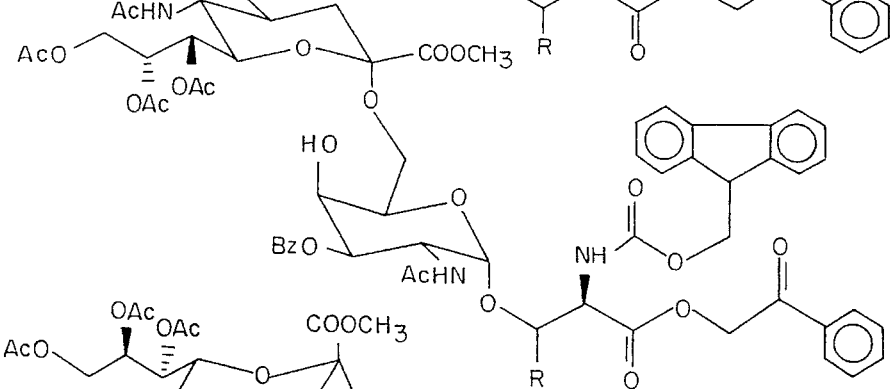
Figure 6C:
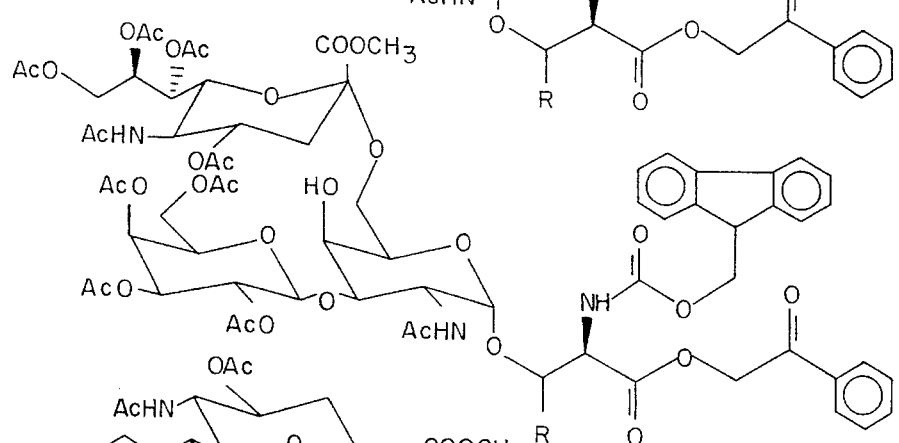
Figure 6D:
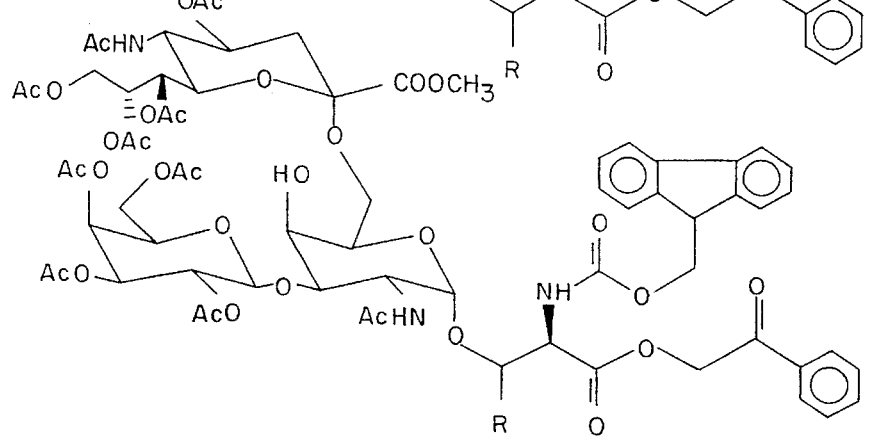
Figures 1, 7A:
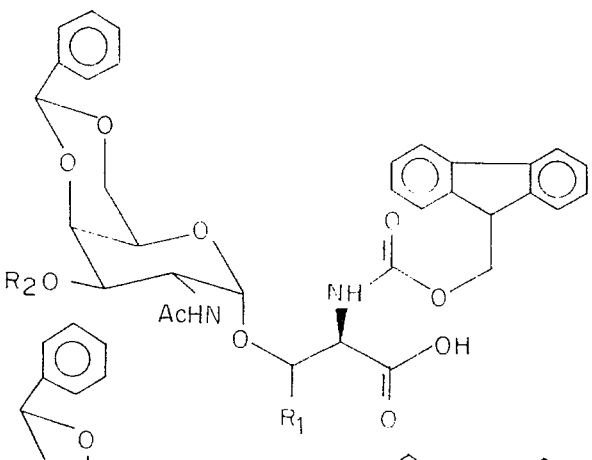
Figures 2, 7A:
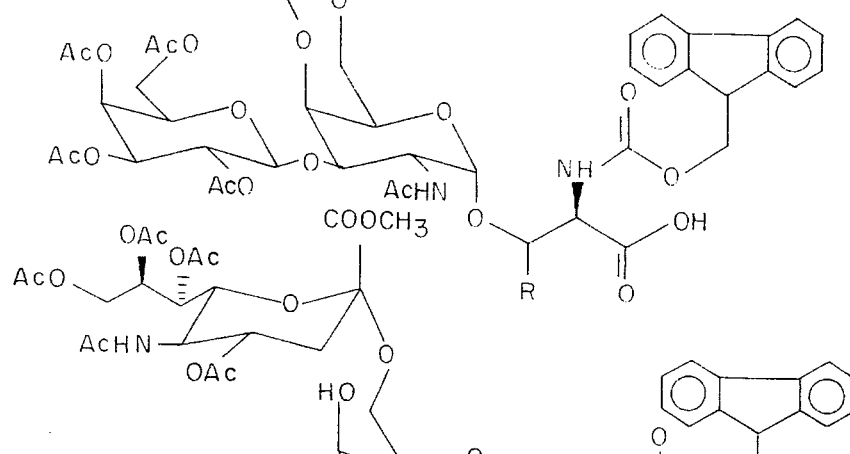
Figures 3, 7A:
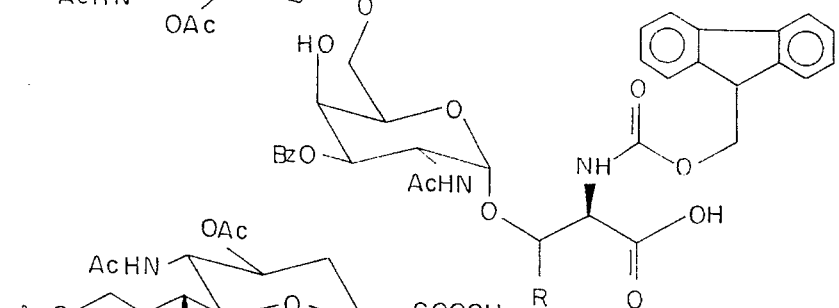
Figures 4, 7A:
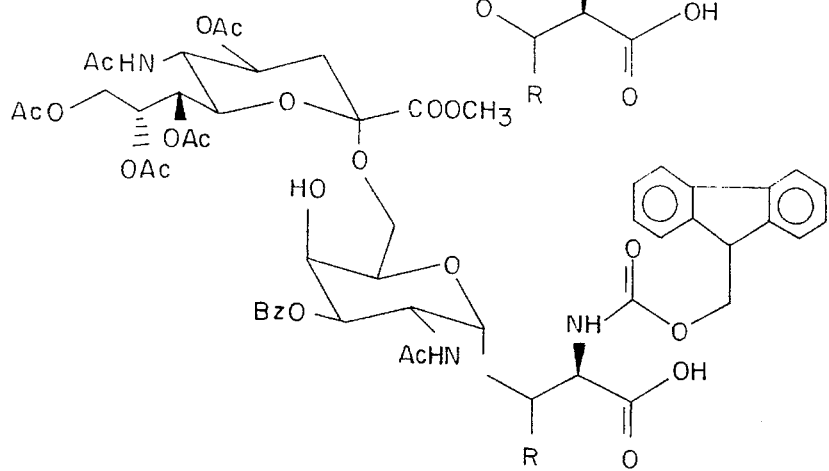
Figures 1, 7B:
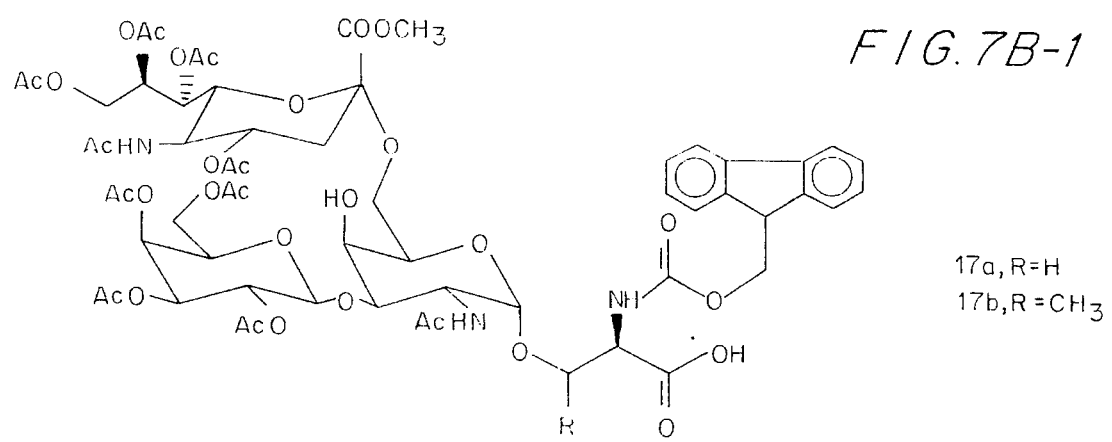
Figures 2, 7B:
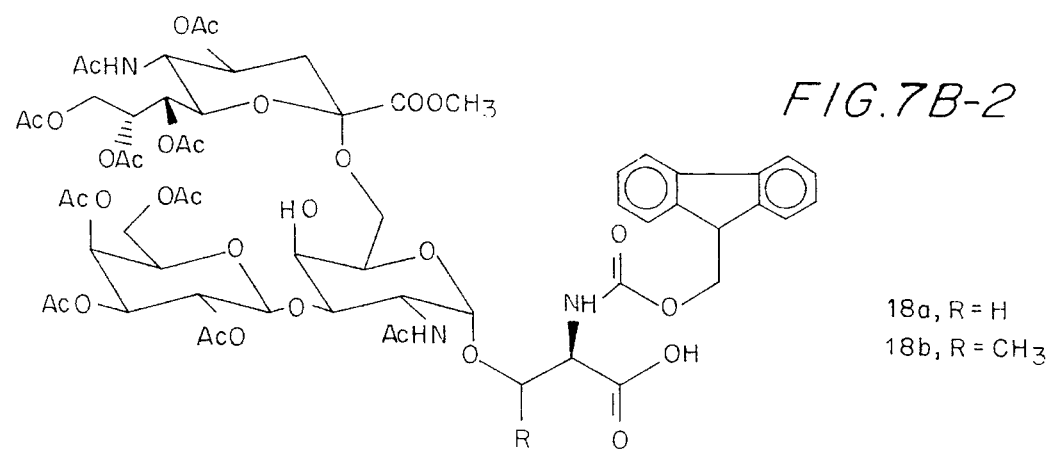
Figures 1, 8A:
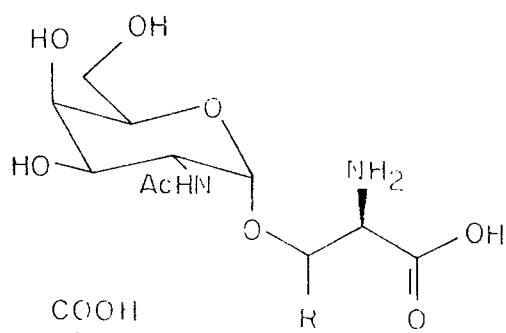
Figures 2, 8A:
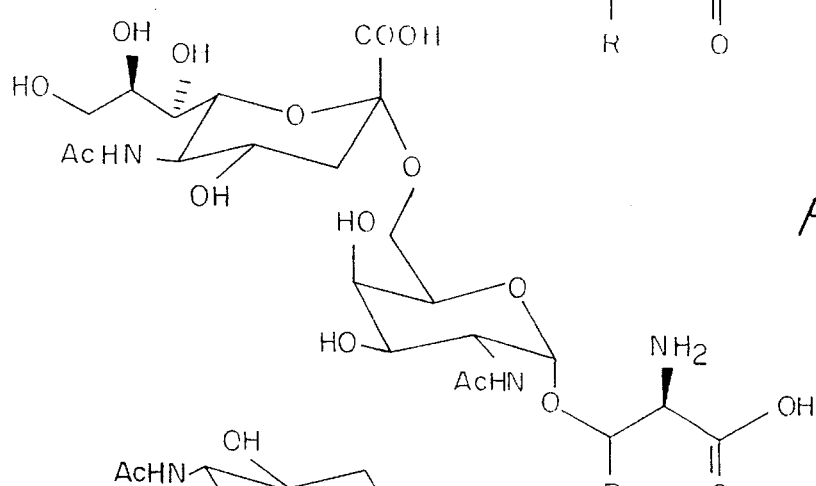
Figures 3, 8A:
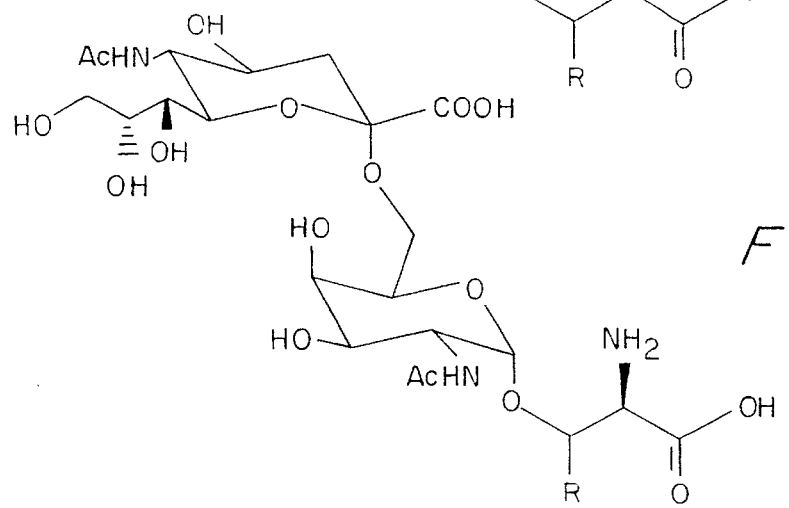
Figures 4, 8A:
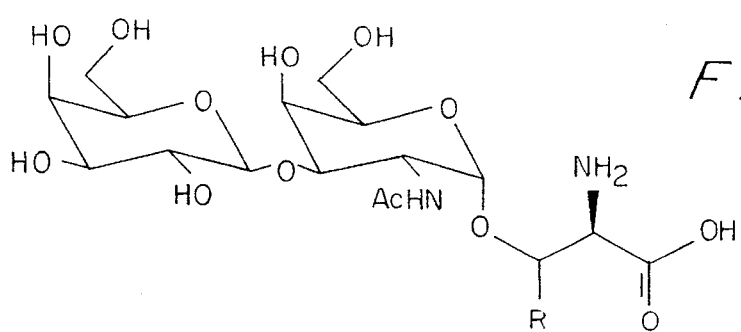
Figures 1, 8B:
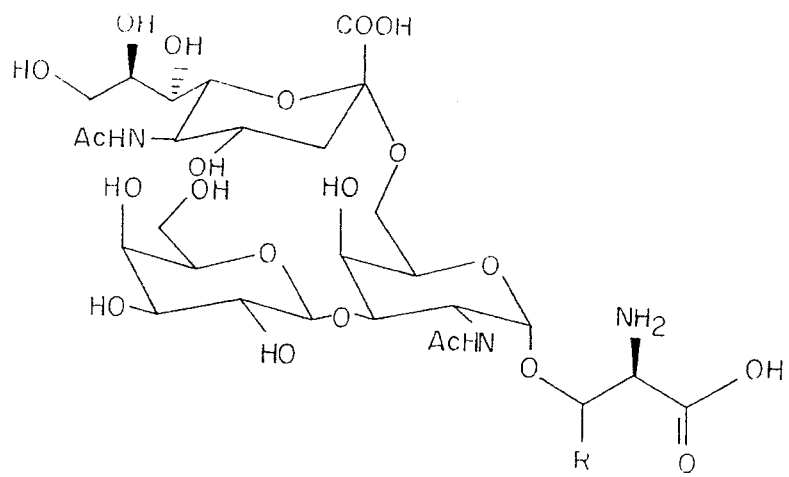
Figures 2, 8B:
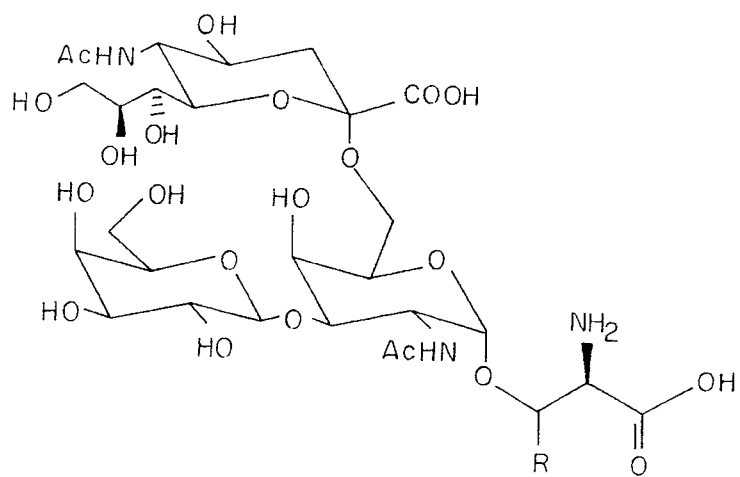
Figure 9A:
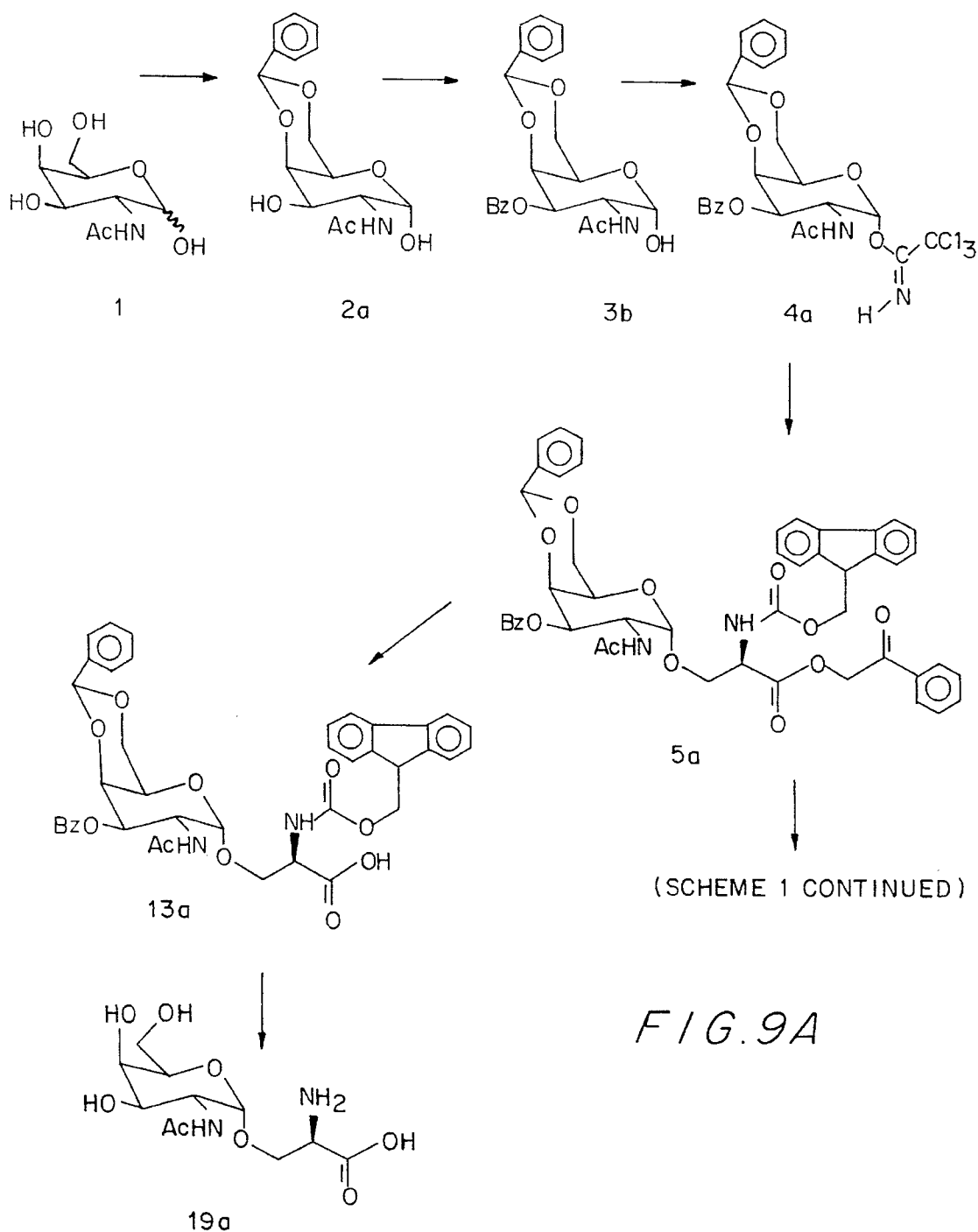
Figure 9B:
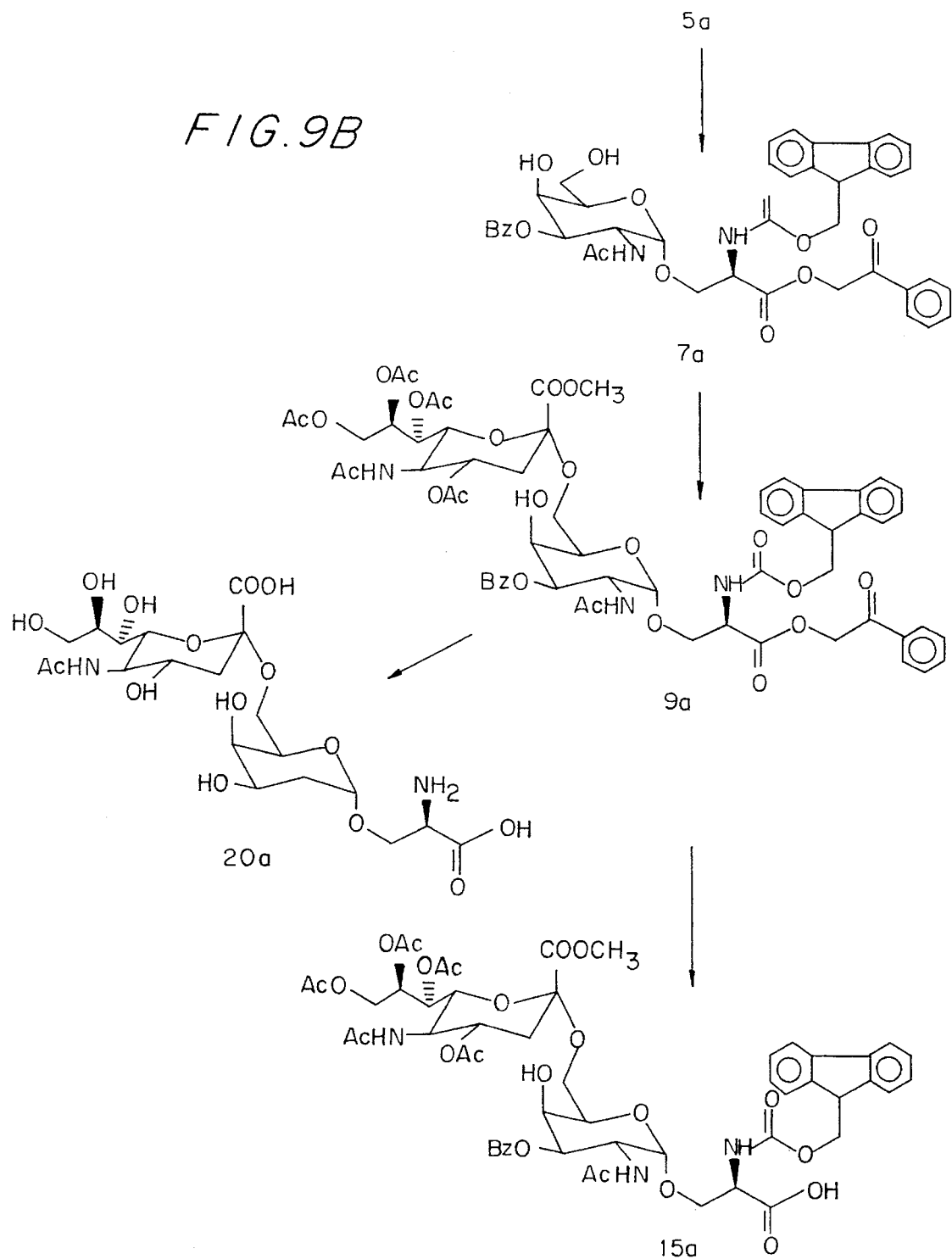
Figure 10A:
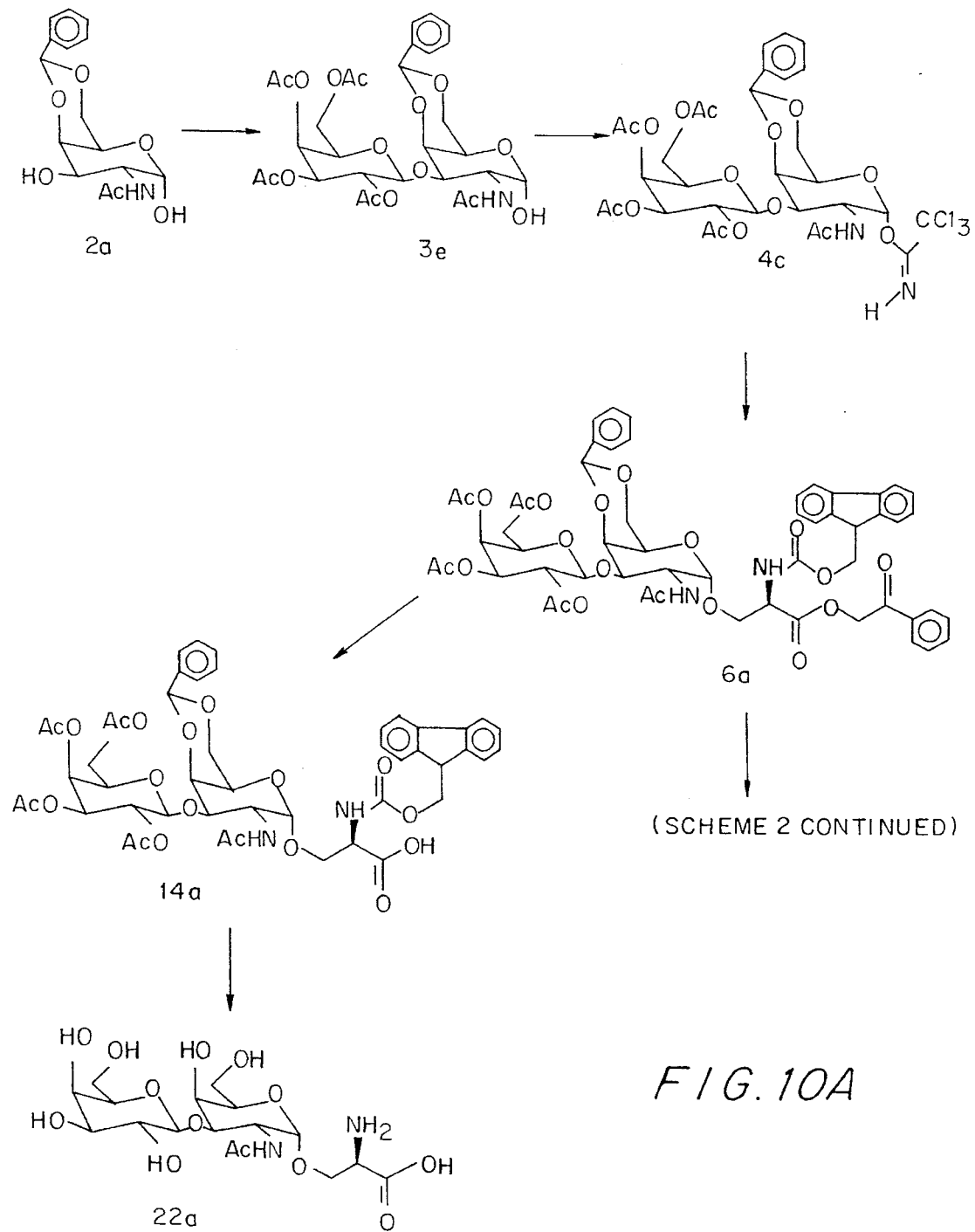
Figure 10B:
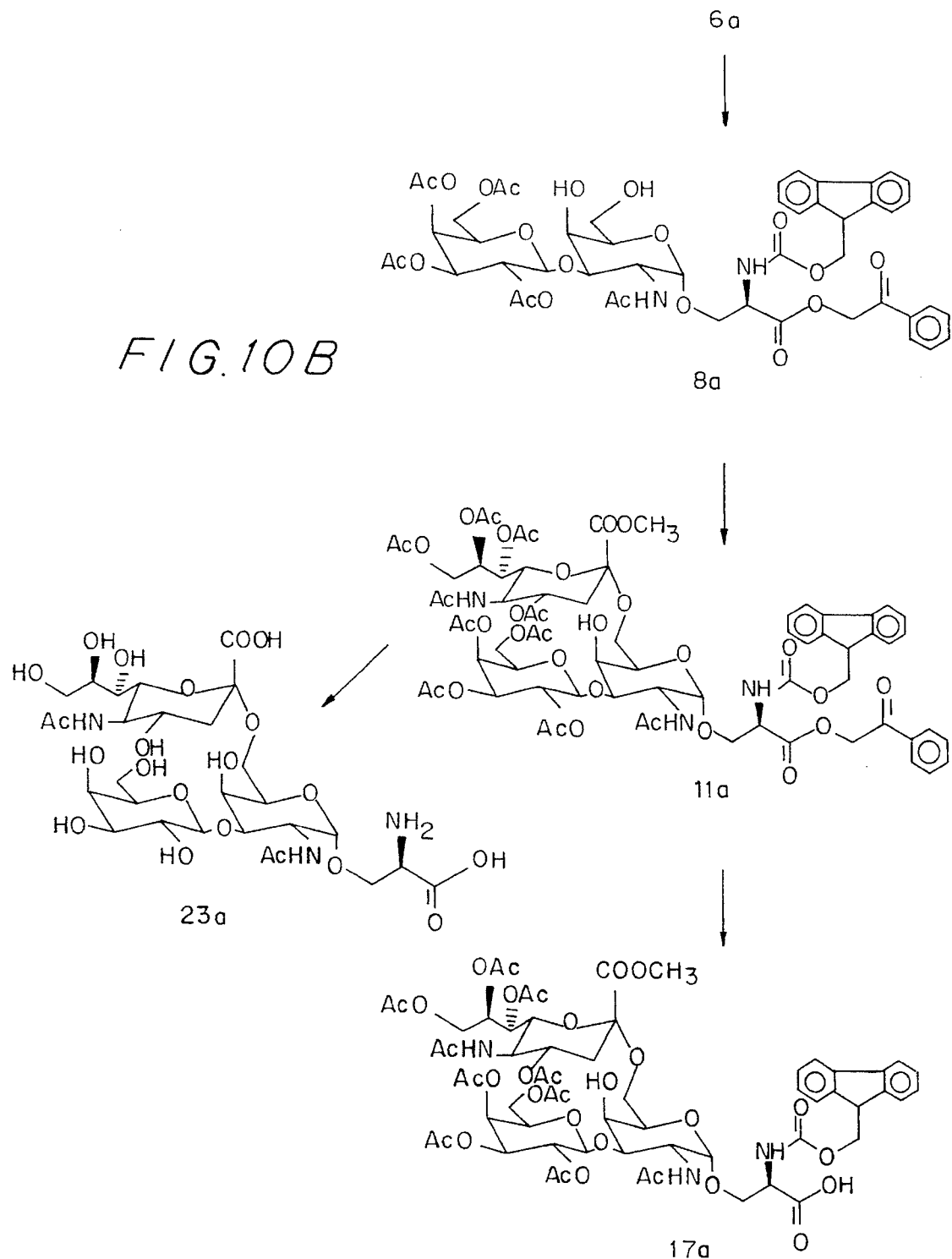
Figure 11A:
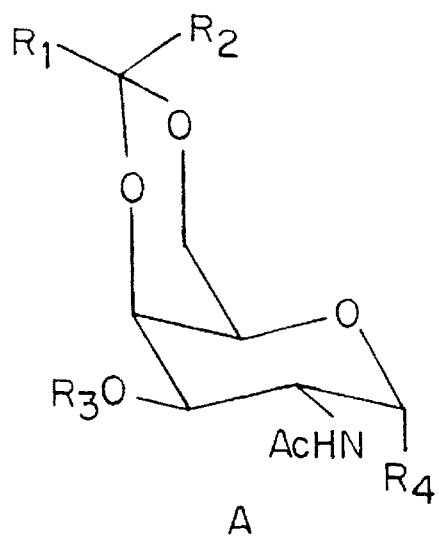
Figure 11B:
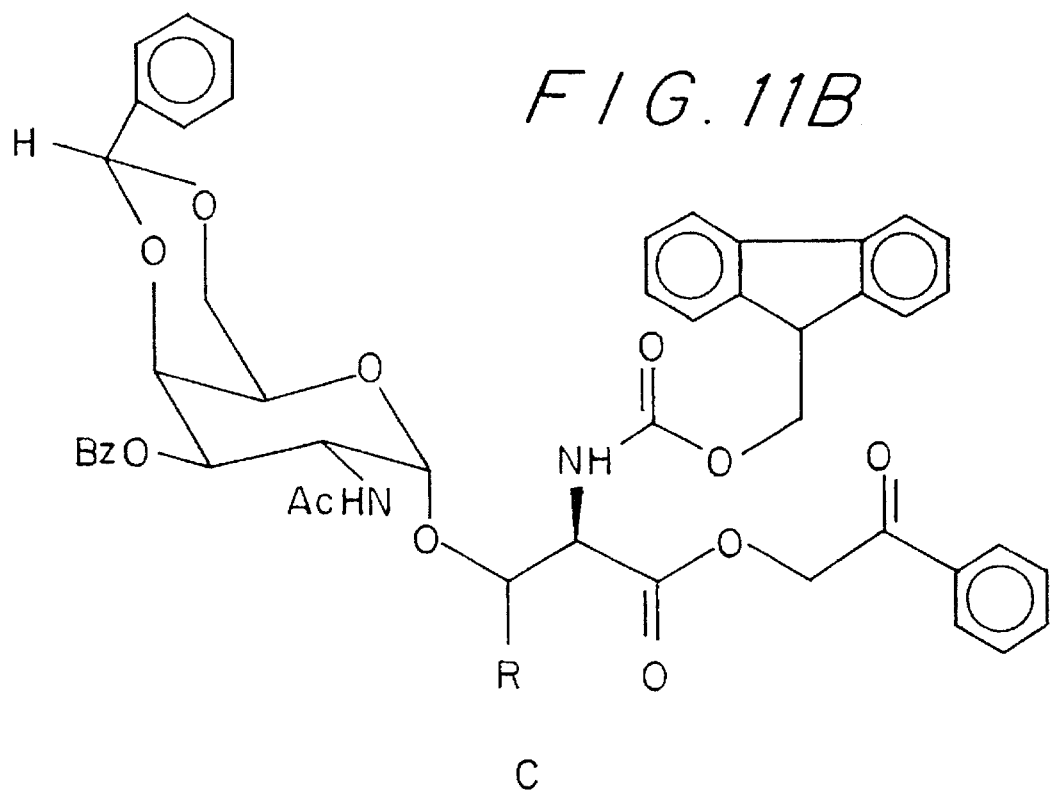

Furthermore, the glycosylamino acid derivatives (FIGS. 4 and 5) are useful in preparing the corresponding intermediates of the sialyl-Tn antiget (STn). Reaction under mildly acidic conditions converts the glycosylamino acid derivatives 5 and 6 into the diol derivatives 7 and 8 by the removal of 4, 6-protecting cyclic acetal/ketal group. The primary 6-OH of the diols may then be selectively glycosylated using glycosyl donors and well known glycosylation methods. For example, suitable glycosyl donors are acetylated pyranosyl halides, such as 5-acetamido, 4,7,8,9-tetra-acetyl, siclyl, chloride ester [donors of GlcNAc, N-acetyl lactosamine celactin can also be used.] The resulting extended carbohydrate amino acid derivatives (9–12) may be processed into glycopeptides as outlined above for monosaccharide amino acids. Using the glycosylated amino acids, such as serine and threonine, synthesized by the methods of disclosure, glycopeptides can be synthesized by their use as building blocks in the F-moc (9-Fluorenyl methoxy carbonyl) based automated peptide synthesis as well as by solid phase batch synthesis manually. Alternatively, glycopeptides can also be synthesized in solution phase using i-butylchloroformate activation. The solid phase synthesis normally employs coupling agents such as dicyclohexyl carbodiimide and an activating agent for the carboxyl group, such as 1-hydroxybenzotriazole (HOBT) or N-Hydroxysuccinimide (NHS). However, there are numerous activating and coupling agents known in the literature which may be used.

The TF-derived glycosylamino acid compounds (14) are used to prepare glycopeptides corresponding to TF-containing mucin epitopes. The TF-derived glycosylamino acid compounds are also useful in preparing the 4,6-O-dealkylidenated derivatives (8). These 4,6-O-dealkylidenated derivatives (8) are glycosylated selectively, which may be processed in the usual manner to yield glycopeptides corresponding to mucin epitopes containing the sialyl-2-6-TF-determinant (Scheme 2).

Thus, the present invention provides versatile commercial methodology for preparing glycosylamino acids corresponding to essential determinants of cancer-associated mucins, particularly the TF, STn and sialyl-2-6-TF determinants (Schemes 1 and 2).

Tn, TF, STn and STF are the structures described in the disclosure. These structures can be bound to any antigenic protein such as Kehole Limpet Hemocyamin (KLH), Diphtheria Toxoid, Tentanus toxoid, Human Serum Albumin (HSA), Bovine Serum Albumin (BSA) etc. Alternatively, as these structures are glycosylated amino acids, antigens may be synthesized in the form of glycosylated peptides which are fragments of tumor associated mucins or glycoproteins.

A variety of well-known tumor associated or normal carbohydrate structures may be synthesized using methodologies discussed herein. The most important are tumor markers such as Tn, TF, STn and STF. These carbohydrate structures can be used to diagnose and image cancer in vitro and in vivo respectively by their used to develop monoclonal antibodies. They can be used to cure cancer by using them for immunization to stimulate the immune system to mount response against malignant cells bearing the same carbohydrate structures.

A variety of carbohydrate structures that are built on the N-acetylgalactosamine are known to be bacterial and viral adhesion ligands. These molecules can be used as antiadhesins to prevent bacterial and viral infection of the cells. Additionally, the glycosylated amino acids can be used for solid phase synthesis of glycoproteins used in biological investigations.

The following nonlimiting examples are included to illustrate the invention:

Experimental 1. 4,6-O-Benzylidenyl, N-acetyl-α-D-galactosamine (2a)

To a suspension of 20 g (90.4 mmol) of N-acetyl-D-galactosamine (1a) in 500 mL of acetonitrile were added benzaldehyde dimethyl acetal (27.14 mL, 180 mmol) and p-toluene sulfonic acid monohydrate (200 mg). The mixture was heated at 60° C. while stirring for three hours. The resultant suspension was filtered. The solid obtained was washed with cold dichloromethane (32 mL) and dried in high vacuum, to obtain 23.1 g (74.7 mmol, 83%) of product. $R_F$=0.36 (9:1, ethyl acetate: methanol); $R_F$=0.14 (10:1 chloroform:methanol), [α]S(23,D)+133° c. 1.0 water), m.p. 168° C. (decomp);

$^1$H-nmr (DMSO-$d_6$+CD$_3$OD) δ=7.35–7.70 (m, 5H, aromatic proton), 5.62 (s, 1H, benzylidene CH), 5.12 (d, 1H, H-1, $J_{1,2}$=3.0 Hz), 4.21 (bd, 1H, H-4, $J_{3,4}$=3.5 Hz), 4.12 (dd, 1H, H-2, $J_{2,3}$=11.0 (m, 2H, H-6a+H-6b), 3.92 (dd, 1H, H-3), 3.85 (bs, 1H, H-5), 1.90 (s, 3H, NHCOCH$_3$); $^{13}$C-nmr (DMSO-$d_6$) δ=169.58 (carbonyl carbon), 138.86, 128.54, 127.85, 126.27 (4 signals of benzylidene aromatic carbons), 99.66 (benzylidene CH carbon) 91.35 (C-1), 75.96 (C-4), 68.95 (C-6), 65.37, 61.95 (C-3 and C-5), 50.27 (C-2), 22.70 (NHAc methyl carbon).

2. 4,6-O-Naphthylidenyl, N-acetyl α-D-galactosamine (2b)

N-acetylgalactosamine (2g) was treated with excess (two equivalents) of 2-naphthaldehyde dimethyl acetal and p-toluene sulfonic acid monohydrate (38 mg) and the reaction was carried out and worked up similar to the preparation of 2a. Crystals (mp 243°–244° C.) were obtained, $R_F$=0.36 (9:1, ethyl acetate: methanol); $R_F$=0.31 (10:1 $CHCl_3$: $CH_3OH$)

$^1$H-nmr (DMSO-$d_6$) δ=8.54–7.40 (m, 7H, naphthylidene aromatic protons), 6.55 (d, 1H, H-1, $J_{1,2}$=3.5 Hz), 6.05 (s, 1H, naphthylidene CH); 5.15–3.80 (m, 11H), 1.80 (s, 3H $NHCOCH_3$).

3. 3-O-Acetyl, 4,6-O-benzylidenyl, N-acetyl α-D-galactosamine (3a)

A solution of acetyl chloride (0.35 mL) in dry methylene chloride (2 mL) was added dropwise with stirring at −25° C. under nitrogen atmosphere to a solution of diol 2a (930 mg, 3.00 mmol), in dry pyridine (10 mL). After one hour, the reaction mixture was quenched with methanol (3 mL) and solvent distilled off, using toluene as co-solvent to get a white solid. It was chromatographed on silica gel and elution with chloroform:methanol (95:5) gave the desired 3-O-acetyl derivative 3a (890 mg, 84.2%):

$^1$H-nmr (CDCl$_3$) δ: 7.5 (m, 2H, Ar) 7.42 (m, 3H, Ar), 6.05 (d, 1H, J =9.5 Hz, NH), 5.5 (s, 1H, benzylidene CH), 5.31 (brs, 1H), 5.17 (dd, 1H, J=3.5 Hz, J=12.5 Hz, H-3), 4.98 (brs, 1H), 4.63 (m, 1H), 4.24 (dd, 1H, J=2.5 Hz, J=12.5 Hz, H-2), 4.07 (d, 1H, J=3.0 Hz, H-4), 3.94 (d, 1H), 3.58 (s, 1H), 2.08 (s, 3H, OAc) and 1.95 (s, 3H, NAc).

4. 3-O-Benzoyl, 4,6-O-benzylidenyl, N-acetyl α-D-galactosamine (3b)

A solution of diol 2a (18.7 g, 60.5 mmol) in a dry pyridine (150 mL) was cooled to −25° C. under nitrogen atmosphere and benzoyl chloride (10.13 g, 72.06 mmol), dissolved in dry methylene chloride (40 mL), was added dropwise over a period of 30 minutes. The reaction was quenched after two hours with methanol (5 mL) and the solvents were distilled off under reduced pressure. The residue was dissolved in methylene chloride and washed with 1N HCl (3×100 mL), saturated sodium bicarbonate (2×100 mL) and water (2×100 mL) and dried over sodium sulphate. The solvent was evaporated and the solid obtained was crystallized from ethyl acetate to afford Compound 3b m.p. 115°–117° C., [α]S(23,D)=182.04:

$^1$H-nmr (CDCl$_3$) δ=8.1 (m, 2H, Ar), 7.32–7.6 (m, 8H, Ar), 6.05 (s, 1H, J=9.5 Hz, NH, exchanges with $D_2O$), 5.36–5.42 (m, 2H), 4.8–4.9 (dd, 2H), 4.25 (dd, 2H), 4.0 (m, 2H), 1.88 (s, 3H, NAc).

5. 3-O-Benzoyl, 4,6-O-benzylidenyl, N-acetyl α-D-galactosaminyl-1-trichloroacetimidate (4a)

To a mixture of 3b (10.0 g, 24.21 mmol) and trichloroacetonitrile (10.48 g, 73.3 mmol) in dry methylene-chloride stirring at 0° C. under nitrogen atmosphere, a solution of 1,8-diazabicyclo[5.4.0]undeca-7-ene (DBU) (Catalytic amount) was added and stirred for two and a half hours. The solvent was distilled off under reduced pressure and the residue was chromatographed on silica gel. Elution with ethylacetate:hexane (7:3) gave the trichloroacetimidate 4a (13.5 g, 98%):

$^1$H-nmr (CDCl$_3$) δ=8.85 (s, 1H, NH), 8.1 (m, 2H, Ar), 7.6–7.4 (m, 8H, Ar), 6.75 (d, 1H, J=3.5 Hz, H-1), 5.65 (d, 1H, J=9.0 Hz, NH), 5.6 (s, 1H, PhCH), 5.5 (dd, 1H, J=3.5 Hz, H-3), 5.15 (m, 1H), 4.6 (d, J=3.0 Hz, 1H), 4.1(dd, 1H, J=2.5 Hz, 13.5 Hz), 4.0 (s, 1H), and 1.9 (s, 3H, NAc).

6. 3-O-Acetyl, 4,6,-O-benzylidenyl, N-acetyl α-D-galactosaminyl-1-chloride (4e)

Compound 2a (1 g, 3.23 mmol) was suspended in 10 mL of redistilled acetyl chloride and the suspension was vigorously stirred in a sealed tube. After 18 hours of stirring, the volatile part of the reaction mixture was evaporated in vacuo at room temperature (20°–24° C.). The foamy residue was taken up in dichloromethane and the solution was repeatedly washed with saturated sodium bicarbonate solution followed by water. The organic layer was separated and dried with anhydrous sodium sulphate. After removal of the solvent in vacuo, the residue was dissolved in ethyl acetate to which hexane was added until crystallization occurred. 640 mg (1.73 mmol) of crystalline solid was obtained $R_F$=0.69 (ethyl acetate); $R_F$=0.59 (10:1 chloroform:methanol).

$^1$H-nmr (CDCl$_3$) δ=7.60–7.35 (m, 5H, benzylidene aromatic protons), 6.42 (d, 1H, H-I, $J_{1,2}$=3.5 Hz), 5.75 (d, 1H, H-4, $J_{NH, H-2}$=8.5 Hz), 5.58 (s, 1H, benzylidene CH), 5.34 (dd, 1H, H-3, $J_{2,3}$=11.5 Hz, $J_{3,4}$=3.2 Hz), 4.98 (m, 1H, H-2), 4.39 (bd, 11 H, H-4), 4.35–4.04 (m, 3H, H-5, H-6a and H-6b), 2.11, 1.98 (2s, 6H, acetyl methyls).

7. 3-O-Acetyl, 4,6-O-benzylidenyl, N-acetylα-D-galactosaminyl-1-fluoride (4f)

To a solution of 3-O-acetyle, 4,6-O-benzylidenyl, N-acetylyl actosamine 3b (1 g, 2.84 mmol) in 25 mL dry dichloromethane cooled to 2°–4° C. was added to a solution of 0.56 mL (4.26 mmol) of diethylamino sulfur trifluoride (DAST) in 5 mL of dichloromethane. The mixture was stirred for one hour. Methanol (5 mL) was added and the mixture was stirred for 10 minutes. The solution was extracted with saturated sodium bicarbonate solution. On evaporation of the solvent, the residue was applied to a column of silica gel and eluted with 1:1 ethyl acetate: hexane. 0.74 g (74%) of 4f was obtained; $R_F$=0.53 (10:10:2 ethyl acetate:hexane:methanol):

$^1$H-nmr (CDCl$_3$) δ=7.60–7.30 (m, 5H, aromatic protons), 5.76 (dd, 1H, H-1, $J_{1,2}$=2.5 Hz, $J_{H-1,F}$=5.3 Hz), 5.54 (s, 1H, benzylidene CH), 5.22 (dd, 1H, H-3, $J_{3,4}$=3.2 Hz, $J_{2,3}$=11.5 Hz), 4.76 (m, 1H, H-2), 4.32 (bd, 1H, H-4), 4.20 (m, 2H, H-6a+H-6b), 3.95 (bs, 1H, H-5), 2.10, 2.00 (2s, 6H acetyl methyl protons).

8. 3-O-Acetyl, 4,6-O-naphthylidenyl, N-acetyl α-D-galactosaminyl-1-chloride (4d)

Compound 2b (4 g) was treated with redistilled acetyl chloride (50 mL) for 40 hours. The mixture was evaporated to dryness. The resultant residue was taken up in ethyl acetate to which was added hexane. Three grams of crystalline 4d were collected. $R_F$=0.68 (ethyl acetate); $R_F$=0.33 (1:1 ethyl acetate/dichloromethane):

$^1$H-nmr (CDCl$_3$) δ=8.25–7.45 (m, 7H, aromatic protons), 6.50 (s, 1H, H-1, $J_{1,2}$=3.5 Hz), 6.10 (s, 1H, naphthylidene CH), 5.72 (d, 1H, NH, $J_{H2-N4}$=8.5 Hz) 6.10 (s, 1H, H-3, $J_{2,3}$=11.2 Hz, $J_{3,4}$=3.5 Hz), 5.01 (m, 1H, H-2), 4.55 (bd, 1H, H-4), 4.30 (m, 2H, H-6a+H-6b), 4.18 (brs, 1H, H-5), 2.12, 1.98 (2s, 6H, acetyl methyl protons).

9. 3-O-Acetyl, 4,6-O-benzylidenyl, N-acetyl α-D-galactosaminyl-1-trichloroacetimidate (4b)

A mixture of 3a (2.0 g, 5.698 mmol) and trichloroacetonitrile (3.28 g, 22.71 mmol) in dry dichloromethane (30 mL) was stirred at 0° C. To the reaction mixture a catalytic among of DBU was added and reaction was followed by TLC. After three hours, the solvents were distilled off and the brown residue was chromatographed on silica gel. Elution with ethylacetate: hexane (7:3) gave the desired trichloroacetamidate 4b (2.5 g, 87.0%)

$^1$H-nmr (CDCl$_3$) δ: 8.8 (s, 1H, NH), 7.6 (m, 2H, Ar), 7.4 (m, 3H, Ar), 6.52 (d, 1H, J=3.5 Hz, H-1α), 5.62 (d, 1H, J=9.0 Hz, NH), 5.57 (s, 1H, benzylidene CH), 5.32 (dd, 1H, J=3.5 Hz, J=11.5 Hz, H-3), 4.50–4.92 (m, 1H), 4.42 (d, 1H, J=2.0 Hz, H-4), 4.35 (dd, 1H, J=2.0, J=12.0 Hz), 4.05 (dd, 1H, J=2.0, J=12.0 Hz), 3.92 (d, 1H, J=1.5 Hz), 2.2 (s, 3H, OAc), 1.95 (s, 3H, NAc); $^{13}$C-nmr δ: 21.05 (OAc), 23.21 (NAc), 96.53 (C-1), 101.01 (benzylidene-CH).

10. 3-O-Benzoyl, 4,6-O-benzyl idenyl, N-acetyl αD-galactosaminyl-1-O-N (Fmoc) Serine Phenacylester (5a)

A mixture of trichloroacetimidate 4a (3.0 g, 5.39 mmol), N-(Fmoc) L-serine phenacylester (5.6 g, 12.58 mmol) and Drierire® (2.0 g) in dry methylene chloride (40 mL) was stirred under a dry nitrogen atmosphere at room temperature for 30 minutes and then cooled to −10° C. To the reaction mixture, a solution of boron trifluoride etherate (0.233 mL, in 40 mL of dry methylene chloride) was added dropwise over a period of 30 minutes. The reaction was followed by TLC (hexane:ethyl acetate 1:1) and after three hours, was quenched with sodium bicarbonate solution (10%, 25 mL). It was filtered over Celite® and washed with methylene chloride. The combined organic extract was washed with water (2×100 mL) and dried over anhydrous sodium sulphate. The solvent was distilled off to obtain a foamy mass which was chromatographed on silica gel and eluted with ethyl acetate:hexane (1:1) to recover unreacted serine linker arm, oxazoline by-product and mixture of glycosides. The crude mixture was again chromatographed and eluted with ethyl acetate:hexane (3:7) to yield the desired α glycoside 5a (950 mg, 23%).

$^1$H-nmr (CDCl$_3$)—7.35–8.1 (m, 24H, Ar), 6.55 (d, 1H, J=9.0 Hz, NH), 5.85 (d, 1H, J=8.5 Hz, NH), 5.63 (d, 1H, J=16.0 Hz, CH$_2$COPh), 5.51 (s, 1H, PhCH), 5.3–5.43 (m, 2H), 5.2 (d, 1H, J=3.5 Hz, H-1), 5.15–5.07 (m, 2H), 4.79 (brs, 1H, Serα-H), 4.2–4.58 (m, 7H), 3.84–3.99 (m, 2H); 1.8 (s, 3H, NAc), $^{13}$C-nmr δ: 99.52 (C-1), 100.76 (PhCH), 155.92 (NHCO), 169.75 (COOCH$_2$), 191.57 (CH$_2$COPh).

11. 3-O-Benzoyl, 4,6-O-benzylidenyl, N-acetyl αD-galactosaminyl-1-O-N (Fmoc) serine (13a)

To a solution of 5a (100 mg, 0.120 mmol) in acetic acid (80%, 10 mL) freshly prepared activated zinc dust (from 2.0 g of zinc dust) was added and the mixture was stirred for 4h at room temperature. It was filtered, inorganic salts washed with aqueous acetic acid (50%, 10 mL ×2), and the solvent from the combined filtrate was distilled off under reduced pressure. The crude product was purified on a Sephadex®-LH-20 Column (ethyl alcohol) to give 13a.

$^1$H-nmr (CD$_3$OD) δ: 8.0 (d, 2H, Ar), 7.75 (d, 2H, Ar), 7.625–7.3 (m, 15H, Ar), 5.50(s, 1H, Ph-CH); 5.45 (br dd, 1H), 4.84 (dd, 1H, J=3.5 Hz, J=12.0 Hz), 4.7 (d, 1H, J=2.5 Hz, H-4), 4.43–4.2 (m, 3H), 4.16–3.9 (m, 6H), 1.89 (s, 3H, NAc) $^{13}$C-nmr δ: 22.90 (CH$_3$CONH) 100.45 (C-1), 101.78 (PhCH).

12. 3-O-Benzoyl, N-acetyl αD-galactosaminyl-1-O-N (Fmoc) serine phenacylester (7a)

A solution of 5a (180 mg) in aqueous acetic acid (80%, 15 mL) was stirred at 80° C. and followed up by TLC (CHCl$_3$:MeOH; 19:1). After two and a half hours, the solvents were distilled under reduced pressure using toluene as a co-solvent and the residue was freeze-dried to get 7a (160 mg). The obtained diol was used for the sialylation reaction without further purification:

$^1$H-nmr (CDCl$_3$) δ: 8.07 (d, 2H, J=8.0 Hz, Ar), 7.83 (d, 2H, J=7.5 Hz, Ar), 7.75 (d, 2H, J=8.0 Hz, Ar), 7.60–7.29 (m, 13H, Ar), 6.64 (d, 1H, J=9.0 Hz, NH, exchanges with D$_2$O), 6.08 (d, 1H, J=8.9 Hz, NH, exchanges with D$_2$O), 5.60 (d, 1H, J=16.5 Hz, CH$_2$COPh), 5.28 (m, 2H, H-3, CH$_2$COPh), 5.10 (d, 1H, J=4.0 Hz, H-1), 5.05 (d, 1H), 4.74 (d, 1H, J=8.5 Hz), 4.48–3.77 (m, 8H), 3.40 (br s, 1H, ¯OH exchanges with D$_2$O), 2.92 (brs, 1H, OH exchanges with D$_2$O) and 1.80 (s, 3H, NAc); $^{13}$C- nmr δ: 23.06 NAc, 54.33 (CH-α), 99.01 (H-1).

13. 3-O-Benzoyl, 6-O-(methyl, 4,3,9-tetra-O-acetyl) α/βsialyl, N-acetyl α-D-galactosaminyl-1-O-N (Fmoc) serine phenacylester (9a and 10a)

A mixture of powdered molecular sieves 4 Å (1.0 g), the diol 7a (500 mg, 0.66 mmol), Hg(CN)$_2$ (6.04 mg, 2.39 mmol) and HgBr$_2$ (431 mg, 1.19 mmol) in methylene chloride (50 mL) was stirred at room temperature for 15 minutes and cooled to 0° C. under a dry nitrogen atmosphere. To the reaction mixture, a solution of 5-acetamido 4,7,8,8,9-tetra-O-acetyl-2-chloro, sialic acid methyl ester (4.7 g, 9.23 mmol) in small portions dissolved in methylene chloride was added while stirring over a period of five days. The mixture was filtered through a Celite® pad, and washed with methylene chloride. The combined filtrate was washed with aqueous solutions of 30% potassium bromide (2×100 mL), 10% EDTA (2×75 mL) and finally with water (2×100 mL), and dried over anhydrous sodium sulphate. The solvent was distilled off to obtain a foamy mass which was chromatographed on silica gel and eluted with ethyl acetate:hexane:methanol (15:10:1) to isolate the α(2–6) glycoside, 9a 170.5 mg) and the β (2–6) glycoside, 10a 275 mg) respectively.

$^1$H-nmr for the α-glycoside 9a CDCl$_3$) δ: 8.1 (d, 2H, J=7.0 Hz, Ar), 7.9–7.32 (m, 17H, Ar), 6.45 (d, 1H, J=9.0 Hz, NH), 5.98 (d, 1H, J=9.0 Hz, NH), 5.43–5.24 (m, 6H), 5.14 (d, 1H, J=3.5 Hz, H-1), 5.0 (m, 1H), 4.82 (m, 2H), 4.5–4.27 (m, 5H), 4.22–4.0 (m, 6H), 3.9–3.7 (m, 6H), 3.65 (br s, 1H exchanges with D$_2$O-OH-4), 2.54 (dd, J=4.5 Hz, J=12.5 Hz, H-3eq), 2.12, 2.09, 1.95, 1.87 and 1.78 (68, 18H, OAc, HNAc); $^{13}$C-nmrδ:98.85 (C-1), 99.05 (C-2').

$^1$H-nmr for the S(2–6) glycoside 10a (CDCl$_3$) δ:8.02–8.08 (d, 2H, J=7.0 Hz, Ar), 7.92–7.3 (m, 17H, Ar), 6.50 (d, 1H, J=8.0 Hz, NH), 6.35 (d, 1H, J=9.0 Hz, NH), 6.26 (d, 1H, J=9.0 Hz, NH), 5.70 (d, 1H, J=16.50 Hz, Ch$_2$COPh), 5.47 (d, 1H, J=16.5 Hz, CH$_2$COPh), 5.42–5.17 (m, 6H), 5.14 (d, 1H, J=3.5 Hz, H-1), 5.01–4.91 (m, 2H), 4.8 (br dd, 1H), 4.45–3.87 (m, 10H), 3.80 (s, 3H, OCH$_3$), 3.73 (dd, 1H), 2.88 (br s, 1H, exchanges with D$_2$O), 2.53 (dd, J$_{3,4}$=4.0 Hz, J=12.5 Hz, H-3eq) 2.13 (s, 3H, Ac), 1.99 (brs, 6H), 1.93 (s, 3H), 1.87 (s, 6H), and 1.78 (dd, 3-H$_{ax}$).

14. 6-O-αSialyl, N-acetyl LD-galactosaminyl-1-O-serine (20a)

To a solution of blocked α(2–6) glycoside 9a (159 mg, 0.129 mmol) in methanol (50 mL), 2% potassium carbonate (25 mL) was added and stirred at room temperature for 24 hours followed by another addition of potassium carbonate (25 mL). Stirring was continued for 20 hours when TLC (n-butanol:ethanol:water 2:1:1) revealed complete absence of the starting compound. To the reaction mixture, acetic anhydride (2–5 mL) was added and stirred overnight. The solvents were distilled off, the residue dissolved in water, the solution extracted with ethyl acetate and the aqueous extract freeze-dried. The crude product was chromatographed on Biogel P-2 to afford 20a (82.5 mg, 99%).

$^1$H-nmr (D$_2$O) δ:4.84 (d, 1H, J=3.50 Hz, H-1), 4.41 (m, 1H, H-4), 4.14 (dd, 1H, J=3.5 Hz, J=12.0 Hz, H-2), 4.05–3.76 (m, 9H), 3.71–3.55 (m, 5H), 2.73 (dd, 1H, J=4.5 Hz, J=12.5 Hz, H-3eq), 2.07 (s, 3H, NHAc), 2.03 (s, 6H, NHAc), 1.66 (dd, 1H, J=12.5 Hz, H-3$_{ax}$).

15. 6-O-βSialyl, N-acetyl α-D-galactosaminyl-1-O-serine (21a)

A mixture of 10a (55 mg, 0.045 mmol) in methanol (25 mL) and potassium carbonate (2%, 25 mL) was stirred at room temperature for 48 hours. To the reaction mixture, acetic anhydride (1.5 mL) was added and stirred for 48 hours. The solvents were evaporated and residue dissolved in water, extracted with ethyl acetate, the aqueous layer was lyophilized and passed on a Biogel P-2 column to get the β(2→6) 21a 20 mg, 70%):

$^1$H-nmr (D$_2$O) δ:4.89 (d, 1H, J=3.50 Hz, H-1), 4.35 (m, 1H), 4.12 (dd, 1H, J=3.5 Hz, J=12.0 Hz), 4.08–3.49 (m, 15H), 2.35 (dd, H, J=4.0 Hz, J=12.5 Hz, H2-3eq) 2.1–2.07 (3s, 9H, NAc), 1.62 (dd, 1H, H-3 ax).

16. 3-O-Acetyl, 4,6,-O-benzylidenyl, N-acetyl α-D-galactosaminyl-1-O-N (Fmoc) threonine phenacylester (5d)

A solution of borontrifluoride etherate (100 μL in 4.0 mL of methylene chloride) was added to a stirred mixture of trichloroacetimidate 4b (2.0 g, 4. 038 mmol), N-Fmoc-threonine phenacylester (3.,6 g, 7.843 mmol), and Drierire® (1.0 g) in dry methylene chloride (25 mL) at −10° C. under nitrogen atmosphere in 30 minutes. The stirring was continued for three hours and the reaction was quenched with aqueous solution of sodium bicarbonate (10%, 25 mL) and the temperature of reaction mixture was raised to room temperature. The organic layer was separated and filtered over Celite® washed with methylene chloride and the combined organic filtrate was washed with water (2×100 mL), dried over sodium sulphate and solvent distilled off to get a foamy mass. It was chromatographed on a silica gel column, eluting with ethylacetate: hexane (1:1) to separate unreacted linker arm, oxazoline byproduct from the glycosides. The glycosides when chromatographed, eluting with chloroform:methanol (100:1), gave the desired 5d (147 mg, 4.5%)

$^1$H-nmr (CDCl$_3$) δ:7.9 (m, 2H, Ar), 7.8 (m, 2H, Ar), 7.58 (m, 15H, Ar), 6.05 (d, 1H, J=9.5 Hz, NH, exchange with D$_2$O), 5.56 (s, 1H, benzylidene CH), 5.54 (d, 1H, J=16.0 Hz, PhCOCH$_2$), 5.43 (d, 1H, J=3.5 Hz, H-1), 5.34 (d, 1H, J=16.0 Hz, PhCOCH$_2$), 5.2 (dd, 1H, J=3.5, J=12 Hz, H-3), 4.85 (dd, 1H, - H-2), 4.6–4.4 (m, 6H), 4.3–4.25 (m, 2H), 4.09 (d, 1H, J=12.0 Hz), 3.85 (brs, 1H), 2.1 (s, 3H, OAc), 1.75 (s, 3H, NAc) and 1.41 (d, 3H, J=6.5 Hz, γ-CH$_3$); $^{13}$C- nmr δ:18.59 (γ-CH$_3$), 21.10 (OAc), 27.99, 47.26, 47.38 (C-2, CHAr$_2$), 58.60 (α-CH), 100.24 (C-1), 101.06 (benzylidene CH), 120.09 –143.87 (Ar), 156.63 (OCONH), 170.13 (CH$_3$COO), 171.55 (CH$_3$CONH), 191.26 (OCH$_2$CO).

17. 3-O-Acetyl, 4,6-O-benzylidenyl, N-acetyl α-D-galactosaminyl-1-O-N (Fmoc) threonine (13d)

A solution of 5d (120 mg in 0.151 mmol) in acetic acid (80%, 10 mL) was added to activated zinc dust (prepared from 800 mg of the zinc dust) and stirred at room temperature for two hours. It was filtered, inorganic salts washed with acetic acid (50%, 2×5 mL), and solvent from the combined filtrate was distilled off under reduced pressure. The crude product was chromatographed on Sephadex LH-20 column to get 13d (82.5 mg, 80.8%) as colorless solid.

$^1$H-nmr (CD$_3$OD), δ: 7.8 (m, 2H, Ar), 7.7 (m, 2H, Ar), 7.5–7.65 (m, 10H, Ar), 5.6 (s, 1H, benzylidene CH), 5.11 (dd, 1H, J=3.5, J=12 Hz, H-3), 5.01 (d, 1H, J=3.5 Hz, H-i), 4.59–4.53 (m, 2H), 4.42 –4.49 (m, 3H), 4.28 (m, 2H), 4.15 (brs, 2H), 3.85 (brs, 1H), 2.05 (s, 3H, OAc), 1.95 (s, 3H, NAc), 1.23 (d, 3H, J=6.0 Hz, γCH$_3$).

The foregoing description of the specific embodiments will so fully reveal the general nature of the invention that others can, by applying current knowledge, readily modify and/or adopt for various applications of such specific embodiments without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation.

| Table of compounds |
| --- |
| 1a. N-Acetyl-D-galactosamine |
| 1b. 3,4,6-0-Triacetyl, N-acetyl-D-galactosaminyl-1-trichloroactimidate |
| 1c. 4,5 (3,4,6-O-Triacetyl, D-galactosyl) 2-methyl-1,3 oxazoline |
| 1d. (N-Fmoc) Serine phenacylester |
| 1e. (N-Fmoc) Threonine phenacylester |
| 2a. 4,6-O-Benzylidenyl, N-acetyl αD-galactosamine |
| 2b. 4,6-O-Naphthylidenyl, N-acetyl αD-galactosamine |
| 2c. 4,6-O-Ethylidenyl, N-acetyl αD-galactosamine |
| 2d. 4,6-O-Isopropylidenyl, N-acetyl αD-galactosamine |
| 2e. 4,6-O-t-Butylidenyl, N-acetyl αD-galactosamine |
| 3a. 3-O-Acetyl, 4,6-O-benzylidenyl, N-acetyl αD-galactosamine |
| 3b. 3-O-Benzoyl, 4,6-O-benzylidenyl, N-acetyl αD-galactosamine |
| 3c. 3-O-Trifluoroacetyl, 4,6-O-benzylidenyl, N-acetyl αD-galactosamine |
| 3d. 3-O-Chloroacetyl, 4,6-O-benzylidenyl, N-acetyl αD-galactosamine |
| 3e. 3-O-(2,3,4,6-Tetra-O-acetyl) D-galactosyl, 4,6-O-benzylidenyl, N-acetyl αD-galactosamine |
| 4a. 3-O-benzoyl, 4,6-O-benzylidenyl, N-acetyl αD-galactosaminyl-1-trichloroacetimidate |
| 4b. 3-O-acetyl, 4,6-O-benzylidenyl, N-acetyl αD-galactosaminyl-1-trichloroacetimidate |
| 4c. 3-O-(2,3,4,6-Tetra-O-acetyl) D-galactosyl,4,6-O-benzylidenyl, N-acetyl αD-galactosaminyl-1-trichloroacetimidate |
| 4d. 3-O-Acetyl, 4,6-O-naphthylidenyl, N-acetyl αD-galactosaminyl-1-chloride |
| 4e. 3-O-Acetyl, 4,6-O-benzylidenyl, N-acetyl αD-galactosaminyl-1-chloride |
| 4f. 3-O-Acetyl, 4,6-O-benzylidenyl, N-acetyl αD-galactosaminyl-1-fluoride |
| 4g. 3-O-Benzoyl, 4,6-O-benzylidenyl N-acetyl αD-galactosaminyl-1-diethylphosphite |
| 4h. 3-O-(2,3,4,6-Tetra-O-acetyl) βD-galactosyl, 4,6-O-benzylidenyl, N-acetyl αD-galactosaminyl-0-N(Fmoc) diethylphosphite |
| 5a. 3-O-Benzoyl, 4,6-O-benzylidenyl, N-acetyl αD-galactosaminyl-1-O-N(Fmoc) serine phenacylester |
| 5b. 3-O-Benzoyl, 4,6-O-benzylidenyl, N-acetyl αD-galactosaminyl-1-N(Fmoc) threonine phenacylester |
| 5c. 3-O-Acetyl, 4,6-O-benzylidenyl, N-acetyl αD-galactosaminyl-1-O-N(Fmoc) serine phenacylester |
| 5d. 3-O-Acetyl, 4,6-O-benzylidenyl, N-acetyl αD-galactosaminyl-1-O-N(Fmoc) threonine phenacylester |
| 6a. 3-O-(2,3,4,6-Tetra-O-acetyl) βD-galactosyl, 4,6-O- |

Table of compounds benzylidenyl, N-acetyl αD-galactosaminyl-1-O-N(Fmoc) serine phenacylester
6b. 3-O-(2,3,4,6-Tetra-O-acetyl) βD-galactosyl, 4,6-O-benzylidenyl, N-acetyl αD-galactosaminyl-1-O-N(Fmoc) threonine phenacylester
7a. 3-O-Benzoyl, N-acetyl αD-galactosaminyl-1-O-N(Fmoc)serine phenacylester
7b. 3-O-Benzoyl, N-acetyl αD-galactosaminyl-1-O-N(Fmoc)threonine phenacylester
7c. 3-O-Acetyl, N-acetyl αD-galactosaminyl-1-O-N(Fmoc)serine phenacylester
7d. 3-O-Acetyl, N-acetyl αD-galactosaminyl-1-O-N(Fmoc)threonine phenacylester
8a. 3-O-(2,3,4,6-Tetra-O-acetyl) βD-galactosyl, N-acetyl αD-galactosaminyl-1-O-N(Fmoc)serine phenacylester
8b. 3-O-(2,3,4,6-Tetra-O-acetyl) βD-galactosyl, N-acetyl αD-galactosaminyl-1-O-N(Fmoc)threonine phenacylester
9a. 3-O-Benzoyl, 6-O- (methyl 4,7,8,9-tetra-O-acetyl) α sialyl, N-acetyl αD-galactosaminyl-1-O-N(Fmoc)serine phenacylester
9b. 3-O-Benzoyl, 6-O-(methyl 4,7,8,9-tetra-O-actyl) ∝ sialyl, N-acetyl ∝D-galactosaminyl-1-O-N(Fmoc)threonine phenacylester
10a. 3-O-Benzoyl, 6-O-(methyl 4,7,8,9-tetra-O-acetyl) β sialyl, N-acetyl αD-galactosaminyll-1-O-N(Fmoc)threonine phenacylester
10b. 3-O-Benzoyl, 6-O-(methyl 4,7,8,9-tetra-O-acetyl) β sialyl, N-acetyl αD-galactosaminyl-1-O-N(Fmoc)serine phenacylester
11a. 3-O-(2,3,4,6-Tetra-O-acetyl) βD-galactosyl, 6-O-(methyl 4,7,8,9-tetra-O-acetyl)-sialyl,N-acetyl αD-galactosaminyl-1-O-N(Fmoc)serine phenacylester
11b. 3-O-(2,3,4,6-Tetra-O-acetyl) βD-galactosyl 6-O-(methyl 4,7,8,9 tetra-O-acetyl) α sialyl, N-acetyl αD-galactosaminyl-1-O-N(Fmoc)threonine phenacylester
12a. 3-O-(2,3,4,6-Tetra-O-acetyl) βD-galactosyl 6-O-(methyl 4,7,8,9-tetra-O-acetyl) β sialyl, N-acetyl αD-galactosaminyl-1-O-N(Fmoc)serine phenacylester
12b. 3-O-(2,3,4,6-Tetra-O-acetyl) βD-galactosyl, 6-O-(methyl 4,6,7,9-tetra-O-acetyl) β sialyl, N-acetyl αD-galactosaminyl-1-O-N(Fmoc)threonine phenacylester
13a. 3-O-Benzoyl, 4,6-O-benzylidenyl, N-acetyl αD-galactosaminyl-1-O-N(Fmoc)serine
13b. 3-O-Benzoyl,4,6,O-benzylidenyl, N-acetyl αD-galactosaminyl-1-O-N(Fmoc)threonine
13c. 3-O-Acetyl,4,6-O-benzylidenyl, N-acetyl αD-galactosaminyl-1-O-N(Fmoc)serine
13d. 3-O-Acetyl, 4,6-O-benzylidenyl, N-acetyl αD-galactosaminyl, 1-O-N(Fmoc)threonine
14a. 3-O-(2,3,4,6-Tetra-O-acetyl) βD-galactosyl, 4,6-O-benzylidenyl, N-acetyl βD-galactosaminyl-1-O-N(Fmoc)serine
14b. 3-O-(2,3,4,6-O-Tetra-O-acetyl) βD-galactosyl, 4,6-O-benzylidenyl, N-acetyl αD-galactosiminyl-1-O-N(Fmoc)threonine
15a. 3-O-Benzoyl, 6-O-(methyl 4,7,8,9-tetra-O-acetyl) α sialyl, N-acetyl αD-galactosaminyl-1-O-N(Fmoc)serine
15b. 3-O-Benzoyl, 6-O-(methyl 4,7,8,9-tetra-O-acetyl) β sialyl, N-acetyl αD-galactosaminyl-1-O-N(Fmoc)threonine
16a. 3-O-Benzoyl, 6-O-(methyl 4,7,8,9-tetra-O-acetyl) β sialyl, N-acetyl αD-galactosaminyl-1-O-N(Fmoc)serine
16b. 3-O-Benzoyl, 6-O-(methyl,4,7,8,9-tetra-O-acetyl) β sialyl, N-acetyl αD-galactosaminyl, 1-O-N(Fmoc)threonine
17a. 3-O-(2,3,4,6-Tetra-O-acetyl) βD-galactosyl,6-O-(methyl 4,7,8,9-tetra-acetyl) α sialyl, N-acetyl αD-galatosaminyl-1-O-N(Fmoc)serine
17b. 3-O-(2,3,4,6-Tetra-O-acetyl) βD-galactosyl, 6-O-(methyl 4,7,8,9 tetra-O-acetyl), α sialyl, N-acetyl αD-galactosaminyl-1-O-N(Fmoc)threonine
18a. 3-O-(2,3,4,6-Tetra-O-acetyl) βD-galactosyl, 6-O-(methyl 4,7,8,9-tetra-O-acetyl), β sialyl, N-acetyl αD-galactosaminyl 1-O-N(Fmoc)serine
18b. 3-O-(2,3,4,6-Tetra-O-acetyl)-D-galactosyl-6-O-(methyl 4,7,8,9-tetra-O-acetyl) β sialyl, N-acetyl αD-galactosaminyl-1-O-N(Fmoc)threonine
19a. N-Acetyl αD-galatosaminyl-1-O-serine
19b. N-Acetyl αD-galctosaminyl-1-O-threonine
20a. 6-O-α Sialyl, N-acetyl αD-galactosaminyl-1-O-serine
20b. 6-O-α Sialyl, N-acetyl αD-galactosaminyl-1-O-threonine
21a. 6-O-β Sialyl, N-acetyl αD-galactosaminyl-1-O-serine
21b. 6-O-β Sialyl, N-acetyl αD-galactosaminyl-1-O-threonine
22a. 3-O-βD-Galactosyl, N-acetyl αD-galactosaminyl-1-O-serine
22b. 3-O-βD-Galactosyl, N-acetyl αD-galactosaminyl-1-O-threonine
23a. 3-O-βD-Galactosyl, 6-O-α sialyl, N-acetyl αD-galactosaminyl-1-O-serine
23b. 3-O-βD-Galactosyl, 6-O-α sialyl, N-acetyl αD-galactosaminyl-1-O-threonine
24a. 3-O-βD-Galactosyl, 6-O-β sialyl, N-acetyl αD-galactosaminyl-1-O-serine
24b. 3-O-βD-Galactosyl, 6-O-β sialyl, N-acetyl αD-galactosaminyl-1-O-threonine

What is claimed is:

1. A process for synthesizing glycosylated amino acids comprising:

reacting N-acetylgalactosamine with a dialkyl acetal of an aldehyde or ketone to form a 4,6-O-alkylidene derivative;

reacting said 4,6-O-alkylidene derivative with a protecting group compound to attach a protecting group selectively to 3-OH of said derivative to form a 3-O-protected derivative;

reacting said 3-O-protected derivative with a suitable reagent to introduce an anomeric group to form a glycosyl donor;

reacting said glycosyl donor with an alcohol to form an N-acetylgalactosaminide.

2. The process according to claim 1 wherein said dialkylacetal is benzaldehyde dimethylacetal.

3. The process according to claim 1 wherein said protecting group is a 3-O-acyl ester.

4. The process according to claim 3 wherein said protecting group is a 3-O-benzoyl ester.

5. The process according to claim 1 wherein said anomeric group is selected from the group consisting of halides, thioether, esters, acetimidate, and trichloroacetimidate.

6. The process according to claim 1 wherein said alcohol is a hydroxyamino acid.

7. The process according to claim 6 wherein the hydroxyamino acid is selected from the group consisting of serine and threonine.

8. The process according to claim 6 wherein the amino and the carboxy group of the hydroxyamino acid are protected with a 9-fluorenylmethoxycarbonyl group or a tert-butoxycarbonyl group.

9. The process according to claim 1 wherein the N-acetylgalactosamine is protected at the 4,6-position by an acetal or ketal forming a six membered ring.

10. The process according to claim 1 wherein said glycosylated amino acid is synthesized in both the α and the β glycoside conformation.

* * * * *